United States Patent
Nothacker et al.

(10) Patent No.: US 10,352,923 B2
(45) Date of Patent: Jul. 16, 2019

(54) METHOD AND SYSTEM FOR REMOTELY MONITORING INTOXICATION

(71) Applicant: KHN Solutions, Inc., San Francisco, CA (US)

(72) Inventors: Keith Harry Nothacker, San Francisco, CA (US); Pauline Anne Basaran, San Francisco, CA (US); Stacey Ilene Rettus, San Francisco, CA (US); Zachary Michael Saul, San Francisco, CA (US)

(73) Assignee: KHN Solutions, Inc., San Francisco, CA (US)

(*) Notice: Subject to any disclaimer, the term of this patent is extended or adjusted under 35 U.S.C. 154(b) by 0 days.

(21) Appl. No.: 15/882,825

(22) Filed: Jan. 29, 2018

(65) Prior Publication Data

US 2018/0164285 A1   Jun. 14, 2018

Related U.S. Application Data

(63) Continuation of application No. 14/973,227, filed on Dec. 17, 2015, now Pat. No. 9,915,644, which is a
(Continued)

(51) Int. Cl.
*G01N 33/497* (2006.01)
*G06K 9/00* (2006.01)

(52) U.S. Cl.
CPC ....... *G01N 33/4972* (2013.01); *G06K 9/0055* (2013.01); *G06K 9/00087* (2013.01);
(Continued)

(58) Field of Classification Search
CPC ............. G01N 33/4972; G01N 33/497; G06K 9/00087; G06K 9/00288; G06K 9/00335;
(Continued)

(56) References Cited

U.S. PATENT DOCUMENTS 4,487,055 A   12/1984   Wolf
4,749,553 A    6/1988   Lopez et al.
(Continued)

FOREIGN PATENT DOCUMENTS

FR   2975522   11/2012

OTHER PUBLICATIONS

FR2975522A1-preview.pdf—English Abstract of FR2975522A1.
STIC Search Results. 15205876-528781-Search Results.pdf.

*Primary Examiner* — Lisa M Caputo
*Assistant Examiner* — Philip L Cotey
(74) *Attorney, Agent, or Firm* — Jeffrey Schox; Diana Lin

(57) ABSTRACT

A method and system for remotely monitoring intoxication of a user, comprising: prompting the user to provide a breath sample at a time point; at a breath sample acquisition device, generating a breath sample signal upon reception of the breath sample from the user, and broadcasting a unique signature proximal in time to the time point; using a sensor of a mobile computing device, generating an authentication signal derived from detection of the unique signature; at a processing system in communication with the mobile computing device and the sample acquisition device, receiving the breath sample signal and the authentication signal; generating a verification assessment that validates provision of the breath sample by the user; determining a value of an intoxication metric for the user based upon the breath sample signal; and transforming the verification assessment and the value of the intoxication metric into an analysis of intoxication of the user.

20 Claims, 10 Drawing Sheets

Related U.S. Application Data continuation of application No. 14/602,919, filed on Jan. 22, 2015, now Pat. No. 9,250,228.

(60) Provisional application No. 61/930,062, filed on Jan. 22, 2014.

(52) U.S. Cl.
CPC ..... *G06K 9/00288* (2013.01); *G06K 9/00335* (2013.01); *G06K 9/00885* (2013.01); *G06K 2009/00939* (2013.01)

(58) Field of Classification Search
CPC ............. G06K 9/0055; G06K 9/00885; G06K 2009/00939; A61B 5/097; A61B 5/082; A61B 5/087; A61B 5/0935
See application file for complete search history.

(56) References Cited

U.S. PATENT DOCUMENTS

| | | |
|---|---|---|
| 4,996,161 A | 2/1991 | Connors et al. |
| D333,441 S | 2/1993 | Greene |
| 5,216,415 A | 6/1993 | Ono et al. |
| 5,291,898 A | 3/1994 | Wolf |
| D362,642 S | 9/1995 | Howse |
| D381,885 S | 8/1997 | Lane |
| 6,433,863 B1 | 8/2002 | Weiss |
| 6,454,723 B1 | 9/2002 | Montagnino |
| 6,556,905 B1 | 4/2003 | Mittelsteadt et al. |
| 6,608,399 B2 | 8/2003 | McConnell et al. |
| 6,726,636 B2 | 4/2004 | Der Ghazarian et al. |
| 6,824,520 B2 | 11/2004 | Orr et al. |
| 6,899,683 B2 | 5/2005 | Mault et al. |
| 6,956,484 B2 | 10/2005 | Crespo |
| D521,885 S | 5/2006 | Eddy et al. |
| D530,424 S | 10/2006 | Manser et al. |
| D539,683 S | 4/2007 | Shaw et al. |
| D539,684 S | 4/2007 | Kitamura et al. |
| 7,204,335 B2 | 4/2007 | Stewart et al. |
| 7,341,693 B2 | 3/2008 | Der Ghazarian et al. |
| 7,451,852 B2 | 11/2008 | Stewart et al. |
| D586,677 S | 2/2009 | Nothacker et al. |
| D603,281 S | 11/2009 | Gonzalez |
| D606,434 S | 12/2009 | Castrodale et al. |
| 7,823,681 B2 | 11/2010 | Crespo et al. |
| 8,040,233 B2 | 10/2011 | Adappa et al. |
| 8,126,735 B2 | 2/2012 | Dicks et al. |
| 8,258,968 B2 | 9/2012 | Ghazarian et al. |
| 8,280,436 B2 | 10/2012 | Harris, Jr. |
| 8,370,027 B2 | 2/2013 | Pettersson et al. |
| 8,381,573 B2 | 2/2013 | Keays |
| 8,453,492 B2 | 6/2013 | Tsuzuki et al. |
| 8,693,597 B2 | 4/2014 | Sexton et al. |
| 8,707,758 B2 | 4/2014 | Keays |
| D705,100 S | 5/2014 | Nothacker et al. |
| 8,808,228 B2 | 8/2014 | Brister et al. |
| 8,814,804 B2 | 8/2014 | Walden et al. |
| 8,849,387 B2 | 9/2014 | Gilbert et al. |
| 8,878,669 B2 | 11/2014 | Nothacker et al. |
| 8,920,725 B2 | 12/2014 | Withrow, III et al. |
| 8,941,501 B1 | 1/2015 | Debijl |
| D724,980 S | 3/2015 | Nothacker et al. |
| D727,763 S | 4/2015 | Nothacker et al. |
| D727,764 S | 4/2015 | Nothacker et al. |
| 9,011,657 B2 * | 4/2015 | Parselle ............ G01N 33/4972 204/403.01 |
| 9,020,773 B2 | 4/2015 | Son et al. |
| D731,341 S | 6/2015 | Kobayakawa |
| 9,045,101 B2 | 6/2015 | Phelan |
| 9,063,120 B2 | 6/2015 | Park |
| 9,076,317 B2 | 7/2015 | Nothacker et al. |
| 9,095,251 B2 | 8/2015 | Purks et al. |
| 9,192,324 B2 | 11/2015 | Phillips et al. |
| 9,192,334 B2 | 11/2015 | Nothacker et al. |
| 9,228,997 B2 | 1/2016 | Keays |
| 9,278,696 B2 | 3/2016 | Yi et al. |
| 9,398,858 B2 | 7/2016 | Phillips et al. |
| 9,417,232 B2 | 8/2016 | Keays et al. |
| 9,481,245 B2 | 11/2016 | Nelson |
| 9,820,114 B2 | 11/2017 | Greenhut et al. |
| 2002/0084130 A1 | 7/2002 | Der et al. |
| 2002/0089660 A1 | 7/2002 | Weiss |
| 2002/0128769 A1 | 9/2002 | Der Ghazarian et al. |
| 2002/0140289 A1 | 10/2002 | McConnell et al. |
| 2002/0143267 A1 | 10/2002 | Montagnino |
| 2003/0028120 A1 | 2/2003 | Mault et al. |
| 2003/0116159 A1 | 6/2003 | Orr et al. |
| 2003/0117287 A1 | 6/2003 | Crespo |
| 2003/0176803 A1 | 9/2003 | Gollar |
| 2006/0217625 A1 | 9/2006 | Forrester, Jr. |
| 2006/0293613 A1 | 12/2006 | Fatehi et al. |
| 2007/0093725 A1 | 4/2007 | I-Hung |
| 2008/0097793 A1 | 4/2008 | Dicks et al. |
| 2008/0262469 A1 | 10/2008 | Brister et al. |
| 2009/0043409 A1 | 2/2009 | Ota |
| 2009/0309711 A1 | 12/2009 | Adappa et al. |
| 2010/0152976 A1 * | 6/2010 | White .................... A61B 5/117 701/48 |
| 2010/0310011 A1 | 12/2010 | Sexton et al. |
| 2011/0079073 A1 | 4/2011 | Keays |
| 2011/0304465 A1 | 12/2011 | Boult et al. |
| 2011/0308297 A1 | 12/2011 | Tsuzuki et al. |
| 2012/0020837 A1 | 1/2012 | Withrow et al. |
| 2012/0132524 A1 * | 5/2012 | Parselle ........... G01N 33/48714 204/403.02 |
| 2012/0157871 A1 | 6/2012 | Walden et al. |
| 2013/0021153 A1 * | 1/2013 | Keays ................ G01N 33/4972 340/539.12 |
| 2013/0035602 A1 | 2/2013 | Gemer |
| 2013/0111979 A1 | 5/2013 | Park |
| 2013/0253360 A1 * | 9/2013 | Wang ................ G01N 33/0047 600/532 |
| 2013/0305808 A1 | 11/2013 | Yoo |
| 2014/0012143 A1 | 1/2014 | Gilbert et al. |
| 2014/0062703 A1 | 3/2014 | Purks et al. |
| 2014/0165698 A1 * | 6/2014 | Mochizuki ......... G01N 33/4972 73/23.3 |
| 2014/0210627 A1 | 7/2014 | Nothacker et al. |
| 2014/0281523 A1 * | 9/2014 | Golino ................ H04L 63/0428 713/168 |
| 2014/0361900 A1 | 12/2014 | Nothacker et al. |
| 2015/0084774 A1 | 3/2015 | Wojcik et al. |
| 2015/0164416 A1 | 6/2015 | Nothacker et al. |

* cited by examiner

Example Unique Signatures
(Single Output Element)

Example Unique Signature
(Multiple Output Elements)

METHOD AND SYSTEM FOR REMOTELY MONITORING INTOXICATION

CROSS-REFERENCE TO RELATED APPLICATIONS

This application is a continuation of U.S. patent application Ser. No. 14/973,227, filed 17 Dec. 2015, which is a continuation of U.S. patent application Ser. No. 14/602,919, filed 22 Jan. 2015, which claims the benefit of U.S. Provisional Application Ser. No. 61/930,062, filed 22 Jan. 2014, which is incorporated in its entirety herein by this reference.

TECHNICAL FIELD

This invention relates generally to the intoxication monitoring device field, and more specifically to a new and useful method and system for remotely monitoring intoxication.

BACKGROUND

It is often desirable to analyze a biological sample from a person to detect substances carried in the biological sample. As such, breathalyzer devices are used to test the content of alcohol (i.e., ethanol) carried in an individual's breath, in order to determine a measure of alcohol consumed by the individual. The measure is typically presented as a blood alcohol content (BAC), which can provide an indication of a user's mental and/or physical adeptness resulting from intoxication. As such, BAC measures are also used to provide a basis for limits of alcohol consumption in relation to the performance of tasks, including driving a vehicle, operating machinery, and performing various tasks in a working environment. While current blood alcohol measuring devices are able to determine an individual's BAC, and are typically used in law enforcement settings, existing systems and methods configured to provide remote monitoring of alcohol consumption, with measures to prevent fraudulent sample provision, are severely limited.

There is thus a need in the intoxication monitoring device field to create a new and useful method and system for remotely monitoring intoxication. This invention provides such a new and useful method and system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Method

Figure 1:
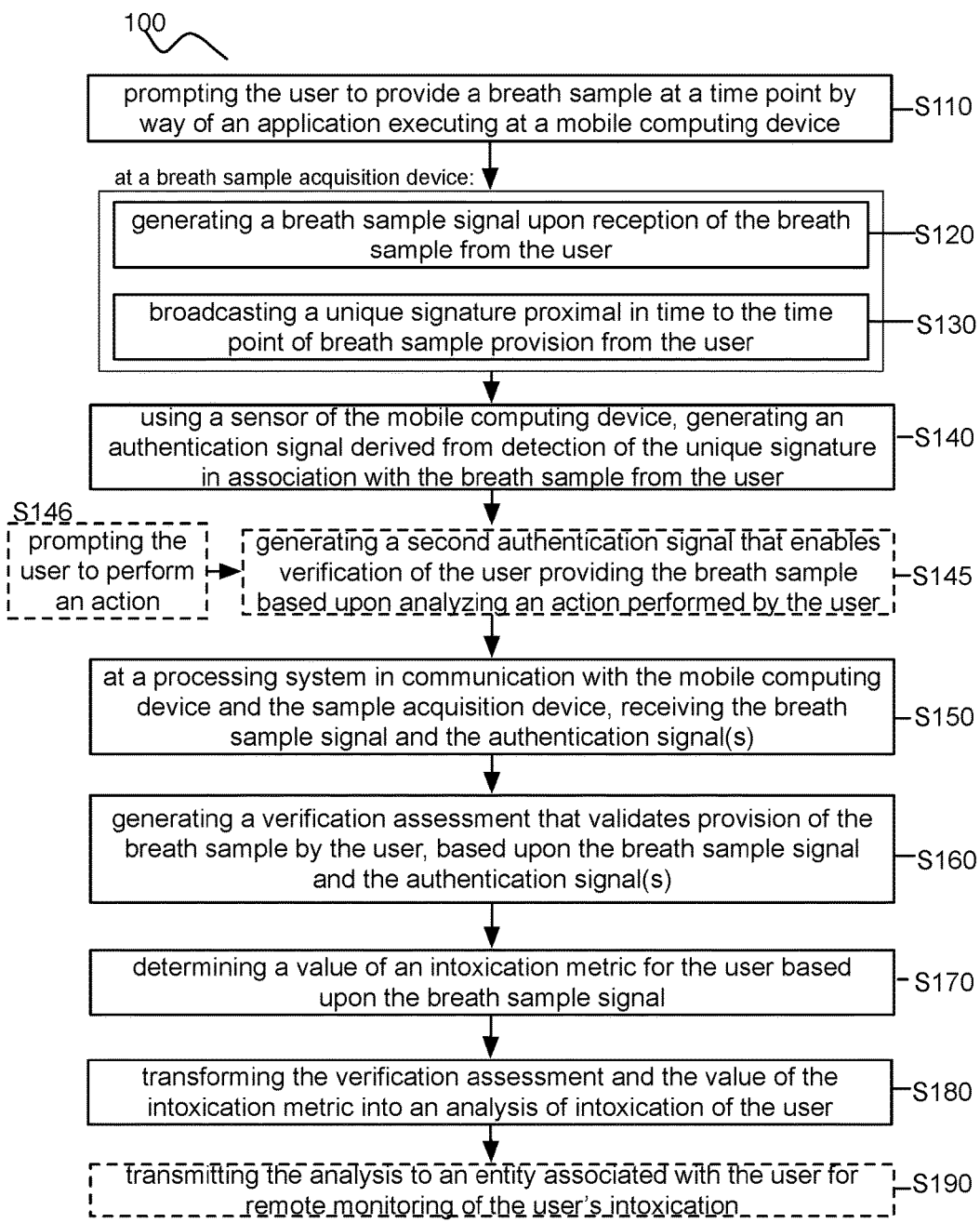
FIG. 1 depicts a flow chart of an embodiment of a method for remotely monitoring intoxication.
Figure 2:
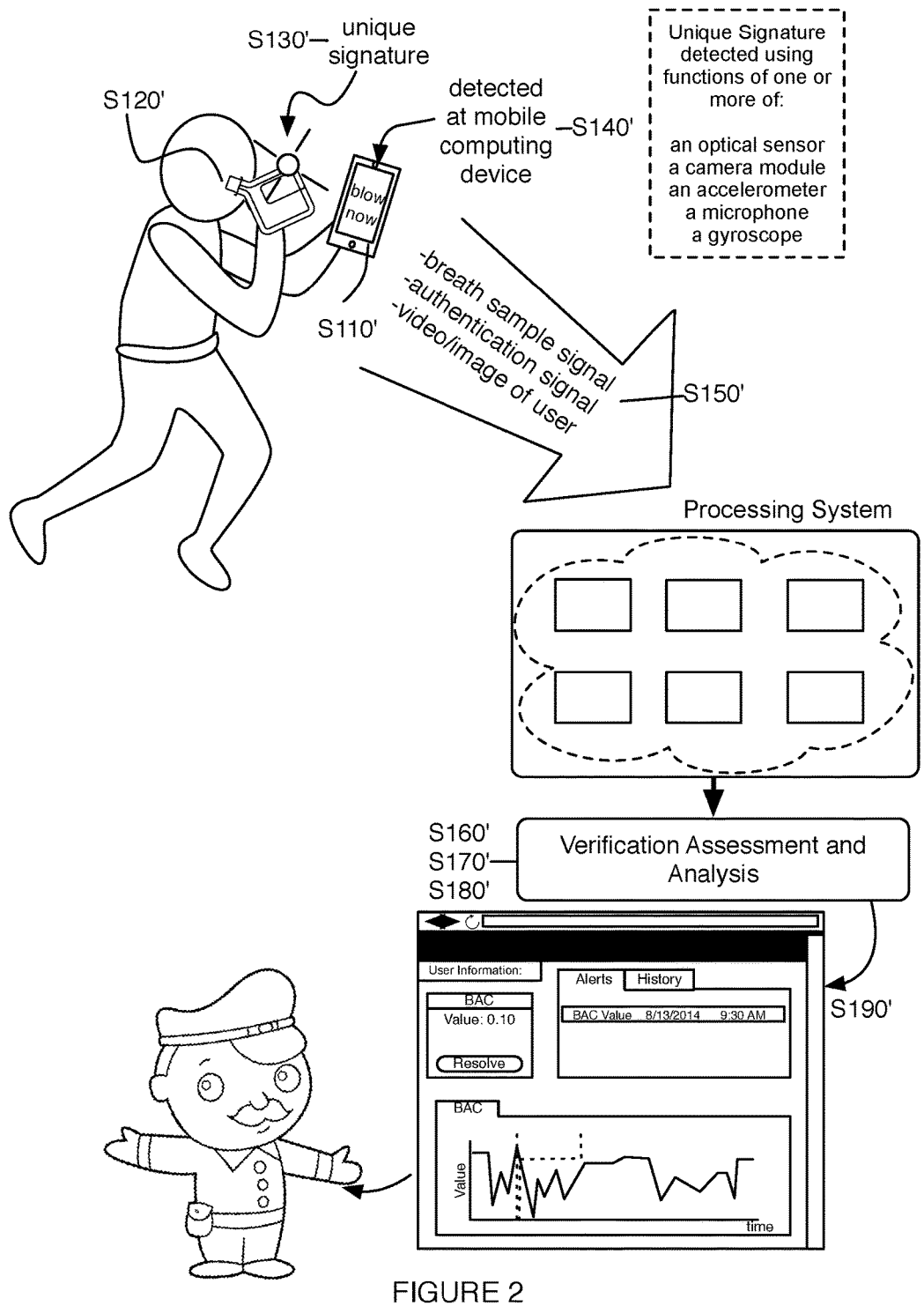
FIG. 2 depicts a schematic of an embodiment of a method for remotely monitoring intoxication.

As shown in FIGS. 1 and 2, an embodiment of a method 100 for remotely monitoring intoxication of a user includes: prompting the user to provide a breath sample at a time point by way of an application executing at a mobile computing device S110; at a breath sample acquisition device, generating a breath sample signal upon reception of the breath sample from the user S120, and broadcasting a unique signature proximal in time to the time point of breath sample provision from the user S130; using a sensor of the mobile computing device, generating an authentication signal derived from detection of the unique signature in association with the breath sample from the user S140; at a processing system in communication with the mobile computing device and the sample acquisition device, receiving the breath sample signal and the authentication signal S150; generating a verification assessment that validates provision of the breath sample by the user, based upon the breath sample signal and the authentication signal S160; determining a value of an intoxication metric for the user based upon the breath sample signal S170; and transforming the verification assessment and the value of the intoxication metric into an analysis of intoxication of the user S180. In some embodiments, the method 100 can include any one or more of generating a second authentication signal that enables verification of the user providing the breath sample based upon analyzing an action performed by the user S145; and transmitting the analysis to an entity associated with the user for remote monitoring of the user's intoxication S190.

The method 100 functions to provide a tool that allows an entity to remotely monitor a user's alcohol consumption/intoxication. As such, the method 100 includes blocks that cooperate to enable verification of the identity of a user providing breath samples indicative of an intoxication state, and to prevent fraudulent sample submission by users attempting to avoid consequences of an intoxication level above a certain limit (e.g., a legal limit). The method 100 preferably enables an entity who is remote from the user to monitor the user's intoxication levels, such that the user does not need to be in the physical presence of the entity monitoring his/her intoxication. In examples, the entity can be a supervisor (e.g., work supervisor, probation officer, etc.), a caretaker, a family member, an acquaintance, or any other suitable entity associated with the user who has an interest in monitoring the user's intoxication. In variations, the method 100 can be implemented by at least a portion of the system 200 described in Section 2 below, but can additionally or alternatively be implemented using any suitable system that facilitates remote monitoring of a user's intoxication.

Block S110 recites: prompting the user to provide a breath sample at a time point by way of an application executing at a mobile computing device, which functions to initiate sample reception and/or user identity verification for remote monitoring of the user's intoxication state. Block S110 is preferably implemented using the mobile computing device associated with the user and the native application installed on the mobile computing device, as described in Section 2 below; however, Block S110 can additionally or alternatively be implemented using any other suitable computing device that can be used to prompt the user to provide a breath sample. In Block S110, prompting is preferably performed using one or more of: display functions of a display of the mobile computing device, speaker functions of an audio-output element of the mobile computing device, haptic functions of an actuation element (e.g., vibration motor) of the mobile computing device, visual signal functions of a light emitting element (e.g., LED) of the mobile computing device and/or the sample acquisition device, and/or any other suitable function of the mobile computing device. In one example, a native application executing at the mobile computing device can provide a graphic and/or textual message, using the display of the mobile computing device, to cue the user to provide a breath sample upon pairing of the mobile computing device with an associated breath sample acquisition device. In a specific example, the native application can implement the display of the mobile computing device to display the breath sample acquisition device that has been paired with the mobile computing device, along with textual messages that indicate an initiation time point of breath sample provision and/or an appropriate duration of breath sample provision, in order to achieve a suitable breath sample. Additionally or alternatively, prompting in Block S110 can be performed using the breath sample acquisition device described in Block S120 and Section 2 below, for instance, using LED signals to prompt sample provision. Additionally or alternatively, prompting in Block S110 can be performed in a non-electronic format, for instance, by way of an interaction (e.g., a verbal interaction, an interaction in writing, etc.) between the user and another human entity associated with the user.

In Block S110, prompting can be triggered by an entity associated with the user, wherein the entity is remotely monitoring the user's intoxication. In one such variation, the entity can provide an input at a control module (e.g., server-coupled control module in communication with the mobile computing device, by way of the native application), wherein the input initiates prompting of the user to provide a breath sample (e.g., immediately, in near real time). In Block S110, prompting can additionally or alternatively be triggered by the user providing the breath sample. In one such variation, the user can provide an input at the mobile computing device (e.g., through the application) and/or the breath sample acquisition device described in further detail below, which indicates that the user desires to provide a sample and initiates prompting of the user to provide the breath sample. Additionally or alternatively, in Block S120 prompting can occur at regular time points (e.g., every morning, every afternoon, every evening, etc.), irregular time points (e.g., preset time points, randomly selected time points), or with any suitable frequency. In a specific example, Block S110 can allow an entity (e.g., a probation officer) supervising the user to submit a request (e.g., to a server facilitating implementation of the method 100) with a schedule for the user to provide breath samples at desired time points. The specific example of Block S110 can then enable automatic prompting of the user to provide breath samples according to the schedule provided by the entity supervising the user. In variations of the specific example, the user can be made aware of the entire schedule created by the supervising entity, or the user can alternatively be unaware of the schedule created by the supervising entity, such that the user cannot anticipate when he/she will be prompted to provide a breath sample.

Additionally or alternatively, in Block S110, prompting can be triggered in association with reception of contextual data derived from one or more sensors of, or other native applications running on the mobile computing device and/or the breath sample acquisition device. In one example, prompting can be triggered upon detection that the user has entered and/or left a location associated with alcohol consumption (e.g., a bar, a lounge, a club, etc.), by using a location identifying element (e.g., GPS module, cell-phone tower triangulation, WiFi triangulation, iBeacon, analysis of a video or image feed, etc.) of the mobile computing device running the native application. In another example, prompting can be triggered upon detection that the user is experienced or has experienced a social event where alcohol (or another impairing substance) could be consumed, by accessing a calendar application of the mobile computing device running the native application. In another example, prompting can be triggered by accessing a log of communication interactions (e.g., text messages, email messages, online social network posts, social check-ins, etc.) facilitated using the mobile computing device. Additionally or alternatively, prompting can be triggered based upon processing signals derived from a wearable biometric sensing device associated with the user and/or the mobile computing device, wherein the signals indicate physiological states of the user associated with impairment. Prompting in Block S110 can, however, be triggered in any other suitable manner.

Block S120 recites: at a breath sample acquisition device in communication with the mobile computing device, generating a breath sample signal upon reception of the breath sample from the user. Block S120 can additionally or alternatively include transmitting a breath sample signal, derived from reception of the breath sample from the user, to the mobile computing device implemented in embodiments of the method 100. Block S120 functions to receive a sample from the user from which a signal can be generated and a value of an intoxication metric can be determined, as in Block S170. Block S120 is preferably implemented using the breath sample acquisition device described in Section 2 below, wherein the breath sample acquisition device is configured to collect breath samples from the user. Preferably, the breath sample acquisition device and the mobile computing device are uniquely associated with each other and with the user, in order to enable verification of the source of breath samples provided by the user. In Block S120, the breath sample signal is preferably generated at a fuel cell sensor that enables measurement of a user's blood alcohol content (BAC), and/or other intoxication metric indicative of sobriety, by an electrochemical process. In relation to the fuel cell sensor, generating the breath sample signal can include producing an electrical current in response to oxidation of alcohol carried in the breath sample provided by the user, wherein the magnitude of the produced electrical current varies in a predictable manner according to the amount (e.g., relative volume) of alcohol carried in the breath sample. In an alternative variation, generating the breath sample signal can be implemented at a semiconductor sensor that produces a change in electrical resistance in response to an alcohol-dioxide reaction, wherein the magnitude of the change in resistance varies in a predictable manner according to the amount (e.g., relative volume) of alcohol carried in the breath sample. In other variations however, Block S120 can additionally or alternatively include generating a breath sample signal at a spectrophotometer configured to produce a signal in response to absorbed or emitted light from alcohol molecules carried in the breath sample from the user. Generating the breath sample signal in Block S120 can, however, include generating a signal at any suitable element configured to respond to alcohol in a sample from the user.

In a specific example, receiving the breath sample can include receiving the breath sample at a cavity of a breathalyzer, wherein the cavity includes a first aperture and a second aperture configured to facilitate breath intake and outflow, respectively. In the specific example, the cavity is in communication with a fuel cell sensor that receives a metered volume of the breath sample, wherein the fuel cell sensor facilitates generation of a breath sample signal by an electrochemical process. Specifically, the fuel cell sensor produces an electrical current in response to oxidation of alcohol carried in the breath sample provided by the user, wherein the magnitude of the produced electrical current varies in a predictable manner according to the amount (e.g., relative volume) of alcohol carried in the breath sample. As such, in the specific example, the breath sample signal comprises an electrical current magnitude that can be detected and processed to determine a value of an intoxication metric indicative of the sobriety of the user. Variations of the specific example can, however, include generation of any other suitable type of electrical signal in response to a received breath sample from the user.

In variations of Blocks S110 and S120 of the method 100, receiving a breath sample from the user can be substituted with or supplemented with receiving any one or more of: urine samples, blood samples, interstitial fluid samples, and any other suitable sample that can be used to assess the user's substance use. Furthermore, in relation to any of the above types of samples, samples used to determine sobriety and substance usage by the user are preferably received from the user in a non-invasive manner; however, samples can additionally or alternatively be received in a minimally invasive or invasive manner. Furthermore, in some variations, a signal generated in response to a received sample can be generated without directly collecting a sample from the user. For example, a signal can be generated in an indirect manner, as derived from an interaction between a stimulus and the user's body (e.g., spectrometer-based analysis of light transmitted from a user's blood vessels).

Block S130 recites: at the breath sample acquisition device in communication with the mobile computing device, broadcasting a unique signature proximal in time to the time point of breath sample provision from the user. Block S130 functions to provide a detectable signature, in association with breath sample provision by the user, that can be used to validate the breath sample acquisition device as the source of the breath sample signal generated in Block S120 and for reception at the processing system in Block S150. In combination with a second authentication signal generated in Block S145, an authentication signal derived from the unique signature of Block S130 can be used to validate the breath sample acquisition device as the source of the breath sample provided by the user, as well as the identity of the user providing the breath sample. As such, fraudulent activity involving another entity (e.g., an entity who is not the user) and/or another breath sample acquisition device is prevented. In Block S130, the mobile computing device and the sample acquisition device are preferably physically uncoupled (e.g., in wireless communication) during broadcasting of the unique signature, such that Block S130 does not require physical coupling between the mobile computing device and the sample acquisition device. However, the mobile computing device and the sample acquisition device can alternatively be in any other suitable configuration.

Figure 3A:
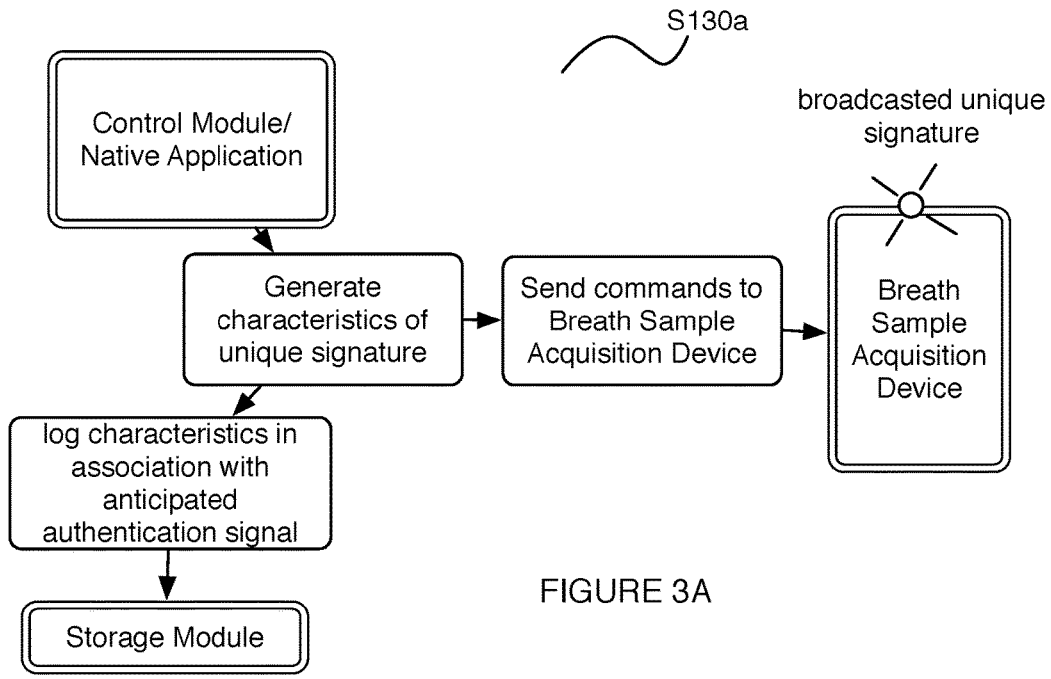
FIGS. 3A and 3B depict variations of a portion of a method for remotely monitoring intoxication.
Figure 3B:
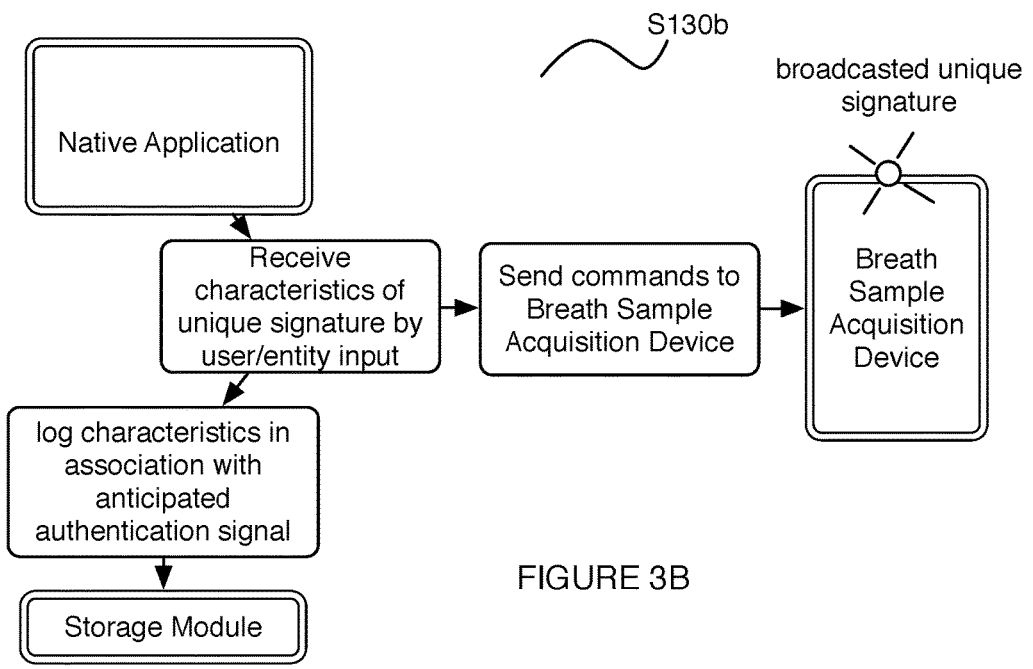

In Block S130, characteristics of the unique signature are preferably logged in anticipation of reception of the associated breath sample signal, such that validation of the unique signature in association with the breath sample and the user, during post-processing of data derived from detection of the unique signature and received signals, can be performed. As such, in one such variation, as shown in FIG. 3A, the native application executing at the mobile computing device can automatically generate and log the characteristics of the unique signature, transmit commands to the sample acquisition device to broadcast the unique signature (e.g., by Bluetooth coupling), and detect/verify the unique signature broadcasted by the sample acquisition device. In another variation, also shown in FIG. 3A, a control module separate from the mobile computing device can generate and log the characteristics of the unique signature, transmit commands to the sample acquisition device to broadcast the unique signature, and facilitate detection of the unique signature broadcasted by the sample acquisition device. Alternatively, the user or another entity can control characteristics of the unique signature. In one such variation, as shown in FIG. 3B, the user can provide inputs using the native application executing at the mobile computing device, wherein the characteristics of the unique signature are logged. The characteristics can then be translated into commands for the sample acquisition device to broadcast the unique signature, and detection of the unique signature broadcasted by the sample acquisition device can be implemented using the mobile computing device. In a specific example, the user can tap and/or drag across a touch interface of the mobile computing device to define characteristics of a unique signature of light emission, and the characteristics can then be transmitted as commands to the sample acquisition device for later verification of a match between the anticipated unique signature and the detected unique signature. However, determination of a match between the anticipated unique signature and data derived from the detected unique signature can alternatively be performed in any other suitable manner. For instance, in still another variation, the sample acquisition device can generate the unique signature, broadcast parameters of the unique signature (e.g., by Bluetooth coupling), and also broadcast the unique signature (e.g., using light emission as described below) for reception at the mobile computing device, thereby enabling verification of the breath sample from the user.

The unique signature provided in Block S130 is preferably detectable using sensors of the mobile computing device associated with the user and the breath sample acquisition device used during provision of the breath sample. Furthermore, detection of the unique signature using the mobile computing device preferably does not require physical coupling between the mobile computing device and the sample acquisition device. Even further, the unique signature provided in Block S130 is preferably detectable using the same sensors of the mobile computing device used to generate the second authentication signals that enable verification of the identity of the user providing the breath sample (e.g., a camera that enables visual identification of the user), such that simultaneous verification of the breath sample source and the identity of the user providing the breath sample can be performed; however, the unique signature can alternatively be detectable in any other suitable manner.

Figure 4A:
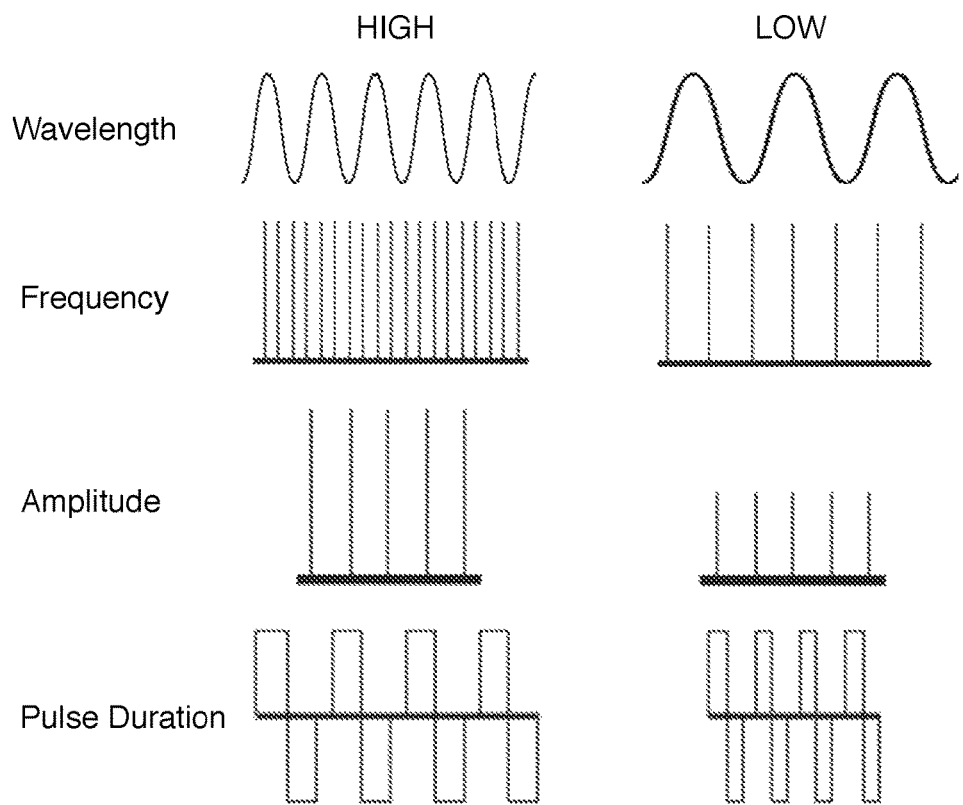
FIGS. 4A and 4B depict variations of unique signatures in an embodiment of a method for remotely monitoring intoxication.
Figure 4B:
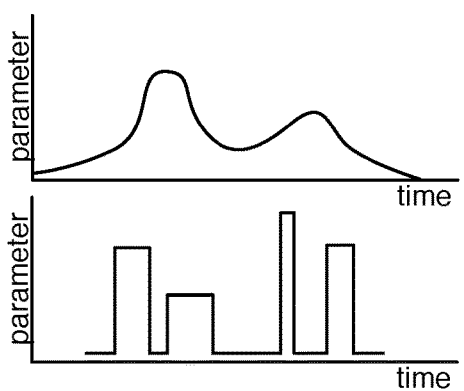
Figure 4B:
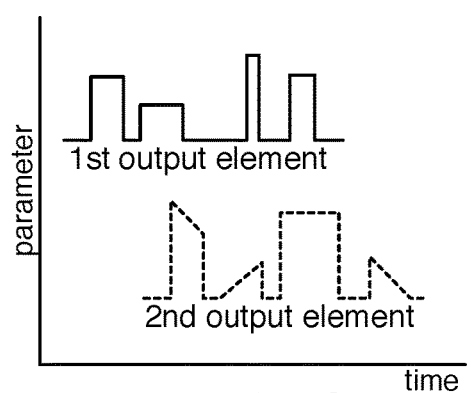

In one variation, the unique signature can comprise a unique signature of light emission using one or more light emitting elements of the sample acquisition device, wherein the unique signature of light emission is detectable using optical sensors (e.g., of a camera module, of a video camera module, of a stereo camera module) of the mobile computing device in communication with the sample acquisition device. In this variation, the characteristics of the unique signature can be automatically generated by a control module (e.g., a control module associated with a native application of the mobile computing device, a control module separate from the mobile computing device), or can alternatively be generated by the user or another entity, as described above. Characteristics can be associated with operational modes of output (e.g., on-off states), and/or associated with modulation of parameters of light emission. In this variation, as shown in FIGS. 4A and 4B, the characteristics of the unique signature can comprise any one or more of: a wavelength of light emission (e.g., using infrared light, using light having wavelengths in the visible light spectrum, using any suitable wavelength(s) of electromagnetic emission), an intensity of light emission, a frequency of light flashes, a pulse width of light flashes in a sequence of light flashes, variations in pulse width of light flashes in the sequence of light flashes, intensity of light flashes in the sequence of light flashes, variations in intensity of light flashes in the sequence of light flashes, number of light flashes in the sequence of light flashes, durations of rest between flashes in the sequence of light flashes, a pattern of light emission using multiple light emitting elements of the sample acquisition device, modulation of any light emission parameter (e.g., intensity, wavelength, etc.) of the unique signature, and any other suitable characteristic.

In another variation, the unique signature can comprise a unique signature of audio signals using one or more audio output elements (e.g., speakers) of the sample acquisition device, wherein the unique sequence of audio signals is detectable using an audio signal sensing element (e.g., microphone, stereo microphone) of the mobile computing device in communication with the sample acquisition device. In this variation, the characteristics of the unique signature can be automatically generated by a control module (e.g., a control module associated with a native application of the mobile computing device, a control module separate from the mobile computing device), or can alternatively be generated by the user or another entity, as described above. Characteristics can be associated with operational modes of output (e.g., on-off states), and/or associated with modulation of parameters of audio signal emission. In this variation, the characteristics of the unique signature can comprise any one or more of: a frequency of audio signals, variations in frequency of the audio signals, a melody of the signature of audio signals, a pulse width of pulsed audio signal outputs in the signature of audio signals, variations in pulse width of pulsed audio signal outputs in the signature of audio signals, volume of audio signals in the signature of audio signals, variations in volume of audio signals in the sequence of audio signals, number of pulses in a sequence of pulsed audio signals, durations of rest between pulses in a sequence of pulsed audio signals, a pattern of audio signals broadcasted by multiple audio signal emitting elements of the sample acquisition device, and any other suitable characteristic.

In another variation, the unique signature can comprise a unique signature of haptically detected signals using one or more actuator elements (e.g., vibration motors) of the sample acquisition device, wherein the unique sequence of haptically detected signals is detectable using an haptic signal sensing element (e.g., accelerometer, microphone) of the mobile computing device in communication with the sample acquisition device. In this variation, the characteristics of the unique signature can be automatically generated by a control module (e.g., a control module associated with a native application of the mobile computing device, a control module separate from the mobile computing device), or can alternatively be generated by the user or another entity, as described above. Characteristics can be associated with operational modes of output (e.g., on-off states), and/or associated with modulation of parameters of haptic signal emission. In this variation, the characteristics of the unique signature can comprise any one or more of: a frequency of vibration pulses, variations in frequency of the vibration pulses, a pulse width of vibration pulses in the signature of haptically detected signals, variations in pulse width of vibration pulses in the signature of haptically detected signals, amplitude of pulses in the signature of haptically detected signals, variations in amplitude of pulses in the signature of haptically detected signals, number of pulses in a signature of haptically detected signals, durations of rest between pulses in a signature of haptically detected signals, a pattern of pulses broadcasted by multiple vibration producing elements of the sample acquisition device, and any other suitable characteristic.

In still other variations, the unique signature can comprise any suitable combination of the above types of signatures (e.g., light emission signatures, audio signal signatures, haptic signal signatures, etc.) and/or any other suitable type of signature. Furthermore, in repeat instances of breath sample provision by the user or a population of users, the type of unique signature can be selected (e.g., randomly selected, deliberately selected) from one of a set of unique signature types (e.g., light emission signatures, audio signal signatures, haptic signal signatures, etc.) for each repeat instance of breath sample provision.

Block S140 recites: using a sensor of the mobile computing device, generating an authentication signal derived from detection of the unique signature in association with the breath sample from the user. Block S140 functions to translate a detected unique signature, broadcasted from the sample acquisition device proximal in time to a time point of breath sample provision, into an authentication signal that can be used to validate the sample acquisition device as the source of the breath sample signal generated from the user. As noted above, in generating the authentication signal in Block S140, the mobile computing device is preferably physically uncoupled from the sample acquisition device, but in communication (e.g., wireless communication) with the sample acquisition device, such that Block S140 does not require physical coupling between the mobile computing device and the sample acquisition device. In one such variation, the mobile computing device and the sample acquisition device are wirelessly coupled (e.g., Bluetooth paired) and in proximity of each other, such that the mobile computing device can appropriately detect the broadcasted unique signature. However, in alternative variations, the mobile computing device and the sample acquisition device can be physically coupled in association with Block S140 and/or other blocks of the method 100.

In Block S140, detection of the unique signature can include any one or more of: optical detection of a broadcasted electromagnetic signature (e.g., emitted light signature) using a camera module of the mobile computing device, detection of a broadcasted audio signal signature using a microphone module of the mobile computing device, detection of a broadcasted vibration signature using a vibration detection module (e.g., microphone module, accelerometer, etc.) of the mobile computing device, and detection of any other broadcasted signature using any other suitable module of the mobile computing device or other device. Additionally, in Block S140, generation of the authentication signal can include transformation of one or more of detected electromagnetic signals, audio signals, vibrations signals, and other signals into a dataset that describes one or more of: amplitudes, frequencies, intensities, wavelengths, durations, patterns, pulse widths, rest periods, and any other suitable parameter of the unique signature detected by the mobile computing device.

As shown in FIGS. 1 and 2, the method 100 can include Block S145, which recites: generating a second authentication signal that enables verification of the identity of the user providing the breath sample, based upon analyzing an action performed by the user. Block S145 functions to enable validation of the identity of the user providing the breath sample, in association with the breath sample received at the sample acquisition device. As such, Block S145, in combination with the authentication signal generated in Block S130, enables validation of the identity of the user providing the breath sample and validation of the breath sample acquisition device as the source of the breath sample provided by the user. Thus, fraudulent activity involving another entity (e.g., an entity who is not the user) and/or another breath sample acquisition device is prevented.

In some variations, Block S145 can include prompting the user to perform an action S146, and generating the second authentication signal in response to the user's performance of the action. In some variations, Block S145 is implemented at a user verification module coupled to at least one of a sample receiving module and a sample processing module; however, Block S145 can additionally or alternatively be implemented at sensors of an electronic device (e.g., mobile computing device) configured to pair with at least one of the sample acquisition device and a processing system, as described in Section 2 below.

In some variations, Block S145 can include generating the second authentication signal at an optical sensor (e.g., of a camera module of the mobile computing device) configured to capture a feature of the user (e.g., a feature that enables facial recognition, recognition of the user's eye, recognition of the user's ear, recognition of the user's blood vessel network, and/or recognition of the user's dermatological features) in image data and/or video data as the user provides the breath sample. Additionally or alternatively, Block S145 can include generating the second authentication signal at a reader (e.g., RFID reader, NFC reader, etc.) configured to read an identification chip coupled to (e.g., embedded subcutaneously in) the user. Additionally or alternatively, Block S145 can include generating the second authentication signal at a module configured to accept a biological sample (e.g., a saliva sample) from the user as the user provides the breath sample, which can be used to authenticate the user (e.g., by analyzing the user's DNA or other biological signature). In yet another example, Block S145 can include prompting the user to ingest a substance that can be detected within the breath of the user, and generating the second authentication signal at a sensor configured to verify the presence of the substance within the user's breath as the user provides the breath sample. Furthermore, additional variations can include combinations of the above variations, and/or combinations of the above variations with any other suitable module configured to uniquely identify the user based upon any other suitable user signature.

In some additional examples that include prompting the user to perform an action, Blocks S145 and S146 can include prompting the user to make an audible noise (i.e., the action) as the user provides the breath sample, and can include generating the second authentication signal at an audio sensor configured to detect the user's voice, as a signature, as the user provides the breath sample. In another variation, Block S146 can include prompting the user to hum (i.e., the action) as the user provides the breath sample, and can include generating the second authentication signal at a vibration sensor (e.g., piezoelectric accelerometer) configured to detect the user's hum vibrations, as a signature, as the user provides the breath sample. In another variation, Block S146 can include prompting the user to touch a fingerprint scanner (i.e., the action) in an orientation that would be difficult to duplicate by another entity as the user provides the breath sample, and generating the second authentication signal in association with a fingerprint pattern signature unique to the user.

Block S150 recites: at a processing system in communication with the mobile computing device and the sample acquisition device, receiving the breath sample signal and the authentication signals. Block S150 functions to enable generation of data that can be used to verify the user's identity, and which can be used to determine a value of an intoxication metric for the user, in order to facilitate remote monitoring of the user's intoxication. In Block S150, the processing system can be directly in communication with both the mobile computing device and the sample acquisition device, or can alternatively be in direct communication one device, and indirectly in communication with the other device based upon communication between the devices. The breath sample signal and the authentication signals (i.e., the authentication signal and the second authentication signal) are preferably received at a processing system, such as the processing system described in Section 2 below; however, the breath sample signal and the authentication signals can alternatively be received at any other suitable processing element configured to transform the breath sample signal into a value of an intoxication metric, and to use the authentication signals to validate the breath sample from the user.

In Block S150, the breath sample signal and the authentication signals are preferably received in real-time; however, the breath sample signal and the authentication signals can alternatively be received in non-real-time. Preferably, the breath sample signal and the authentication signals are received simultaneously and matched to each other (e.g., based upon time stamps, based upon association between an anticipated unique signature and a detected unique signature); however, the breath sample signal and the authentication signals can alternatively be tagged with user specific identifiers (e.g., a user id number, a tag associated with the mobile computing device, a tag associated with the sample acquisition device, a tag associated with unique pairing between the mobile computing device and the sample acquisition device, etc.), received non simultaneously, and/or matched to each other after reception of the breath sample signal and the authentication signals. In a specific example of Block S150, the breath sample signal and the authentication signals can be received wirelessly using one or more Bluetooth transmission modules incorporated into the sample acquisition device (e.g., a breathalyzer) configured to collect a breath sample from a user, and a user verification module configured to generate the authentication signals. However, in variations of the specific example, the breath sample signal and/or the authentication signals can be received at the processing system using any other suitable wireless data link (e.g., 3G connection, 4G connection, WiFi connection, NFC connection, etc.) or wired data link (e.g., audio jack connection, USB connection, lightning cable connection, etc.).

Block S160 recites: generating a verification assessment that validates provision of the breath sample by the user, based upon the breath sample signal and the authentication signal. Block S160 functions to provide a qualitative and/or a quantitative assessment of a match between the authentication signals (i.e., the authentication signal that enables validation of the breath sample source and the second authentication signal that enables validation of the identity of the user providing the breath sample) and a known identifying signature of the user. The verification assessment also preferably accounts for a time elapsed between provision of the breath sample, as determined from the breath sample signal, and generation of the authentication signals, in order to support a determination that the user actually provided the breath sample. In relation to the authentication signal that enables validation of the source (i.e., the sample acquisition device as the source) of the breath sample, the verification assessment can include one or more of: comparing a signature of detected emitted light broadcasted by the sample acquisition device to the anticipated unique signature of light emission, comparing a signature of detected audio signals broadcasted by the sample acquisition device to the anticipated unique signature of audio signals, comparing a signature of detected vibration signals broadcasted by the sample acquisition device to the anticipated unique signature of vibration signals, and comparing any other suitable detected authentication signal to an anticipated signature to validate the source of the provided breath sample.

In relation to the second authentication signal that enables validation of the identity of the user providing the breath sample, the verification assessment can include one or more of: comparing at least one of a facial feature signature, an eye signature, and an ear morphology signature to the authentication signals; comparing an audio signature of the user to the authentication signals; comparing a vibration signature of the user to the authentication signals; comparing a fingerprint signature of the user to the authentication signals; comparing an identification chip signature of the user to the authentication signals; comparing a biological signature of the user to the authentication signals; and comparing a signature of the user from an ingested substance to the authentication signatures.

As such, Block S160 can include performing a template matching algorithm and/or any other suitable matching algorithm, along with statistical methods to assess closeness of matching, in order to verify a match between the anticipated and detected authentication signal, as well as a match between the identity of the user in relation to the second authentication signal. The template matching algorithm(s) can be used to examine similarities and/or differences between the authentication signals and the identifying signature of the user. A matching threshold (e.g., based upon a percent match, etc.) can then be used to generate an assessment of similarity between the authentication signals and a suitable identifying signature (e.g., anticipated unique signature, identity-related signature of the user, etc.). In variations wherein the verification assessment is qualitative, the verification assessment can provide a binary indication of authentication (e.g., the verification assessment indicates that the user's identity was verified from the authentication signals, or the verification assessment indicates that the user's identity was not verified from the authentication signals). In variations wherein the verification assessment is quantitative, the verification assessment can provide a metric that indicates closeness of matching, wherein the metric can be compared to a threshold condition to assess a false identity or a positive identity of the user. As such, in a specific example, the metric can provide a percent of matching between the authentication signals and the identifying signature of the user (e.g., there is a 79% match between the user's identifying signature and the authentication signals), with a percent of matching above 75% taken as a positive identification of the user.

Figure 5:
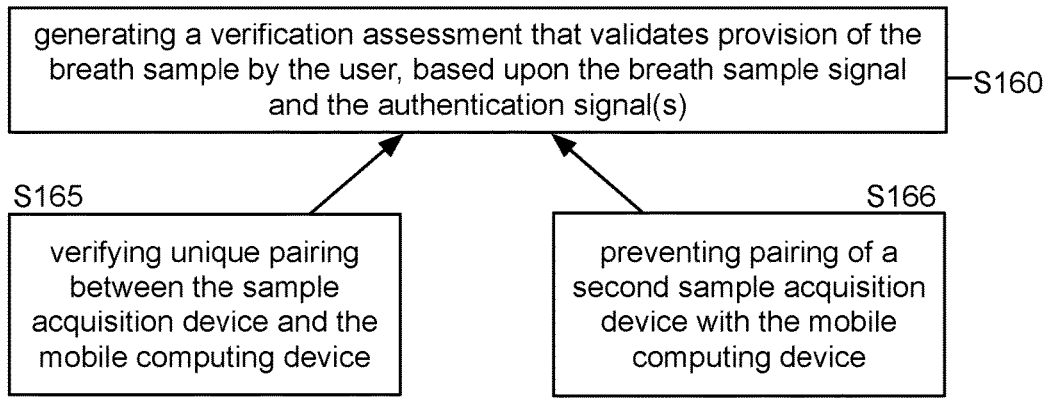
FIG. 5 depicts a variation of an embodiment of a method for remotely monitoring intoxication.

Also noted above and as shown in FIG. 5, Block S160 can be supplemented by Block S165, which recites: verifying unique pairing between the sample acquisition device and the mobile computing device, which functions to provide additional support that validates the source of the breath sample in the verification assessment. In Block S165, a unique mobile computing device identifier (e.g., a device serial number, a mobile equipment identifier, an international mobile station equipment identity) or other identifier (e.g., Wi-Fi address, Bluetooth address, IP address, etc.) can be logged and a unique sample acquisition device identifier (e.g., a device serial number) or other identifier (e.g., Wi-Fi address, Bluetooth address, IP address, etc.) can also be logged for subsequent verification of pairing between approved devices (e.g., a mobile computing device and a sample acquisition device documented to be associated with the user). In variations of Block S165, any breath sample signal and/or authentication signals received at the processing system can be tagged with the sample acquisition device identifier and the mobile computing device identifier and analyzed to verify that the unique sample acquisition device/mobile computing device pair was used to generate and provide the signal(s) to the processing system. In Block S165, verification of unique pairing between the sample acquisition device and the mobile computing device can, however, be performed in any other suitable manner.

Additionally or alternatively, Block S160 can be supplemented by Block S166, which recites: preventing pairing of a second sample acquisition device with the mobile computing device. Block S166 functions to only permit a single unique pairing between the mobile computing device and the sample acquisition device, and to block pairing between multiple sample acquisition devices with the mobile computing device. As such, Block S166 can provide a feature that allows only a single sample acquisition device to be used within proximity of the mobile computing device, in support of prevention of fraudulent sample provision. In one variation, Block S166 can include passing any pairing attempts between sample acquisition devices and the mobile computing device through an approval module (e.g., a software module provided through the native application executing on the mobile computing device). In this variation, the approval module compares an identifier of a device attempting to pair with the mobile computing device to an approved sample acquisition device identifier (e.g., a device serial number, Wi-Fi address, Bluetooth address, etc.) of the sample acquisition device known to be associated with the user. Additionally or alternatively, Block S166 can include preventing pairing between another sample acquisition device and the mobile computing device, once the approved sample acquisition device associated with the user has been paired with the mobile computing device.

In support of the verification assessment, Block S160 can additionally or alternatively include one or more of: verification of a time stamp of sample provision, verification of a time stamp of pairing between the mobile computing device and the sample acquisition device associated with the user, verification of a time stamp of broadcast of the unique signature in relation to a time stamp of detection of the unique signature, and any other suitable verification step that supports validation of the source of the breath sample and validation of the identity of the user providing the breath sample.

Block S170 recites: determining a value of an intoxication metric for the user based upon the breath sample signal, which functions to enable a quantitative analysis of the user's intoxication to be performed. The intoxication metric is preferably a blood alcohol concentration (BAC), which can be determined from the breath sample signal generated as described in relation to Block S120 above; however, the intoxication metric can alternatively be any other suitable metric characterizing intoxication of the user. In variations, a BAC value corresponding to the breath sample can be determined based upon the magnitude of an electrical signal produced when alcohol in the user's breath reacts with a sensing element of the sensor (e.g., a current magnitude produced by a platinum-alcohol oxidation reaction for a fuel cell sensor, a change in electrical resistance produced by an alcohol-dioxide reaction for a semiconductor sensor, etc.). In other variations, a BAC value corresponding to any other suitable type of sample from the user can be determined based upon an electrical signal produced in response to irradiation of the sample (e.g., by way of an electrical pulse generated in response to absorption of infrared light by the sample, using a spectrophotometer), by way of a detected chemical change (e.g., as exhibited by a color change) in response to a chemical reaction between the sample and a chemical additive, or in any other suitable manner.

Figure 6A:
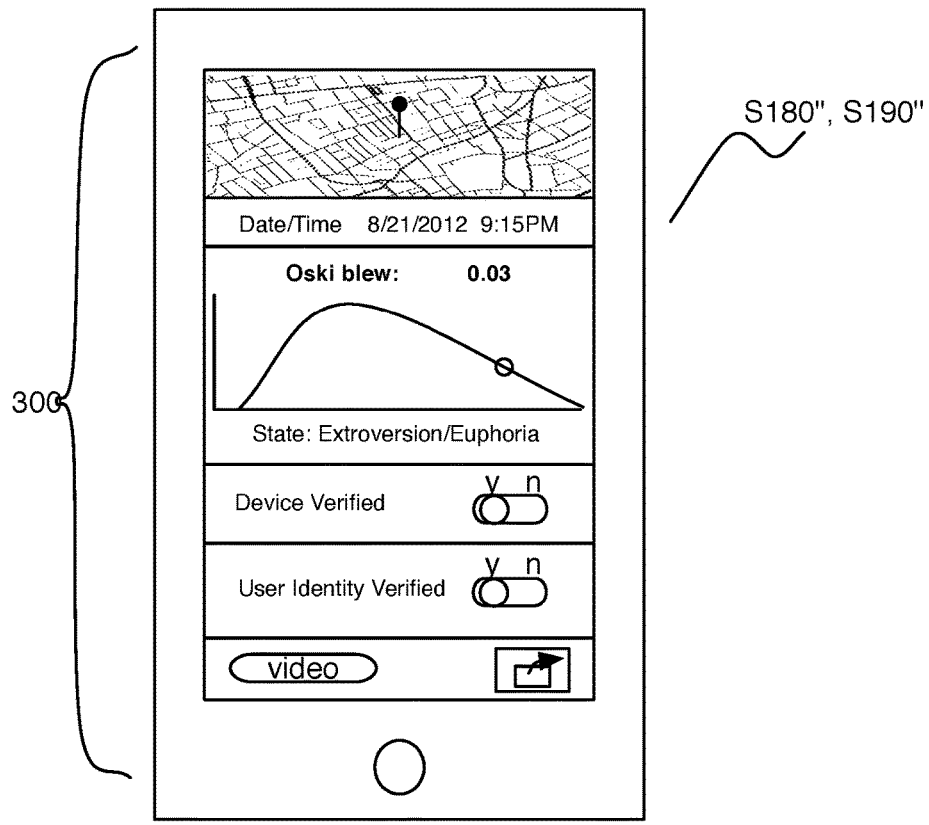
FIGS. 6A and 6B depict examples of a portion of an embodiment a method for remotely monitoring intoxication.
Figure 6B:
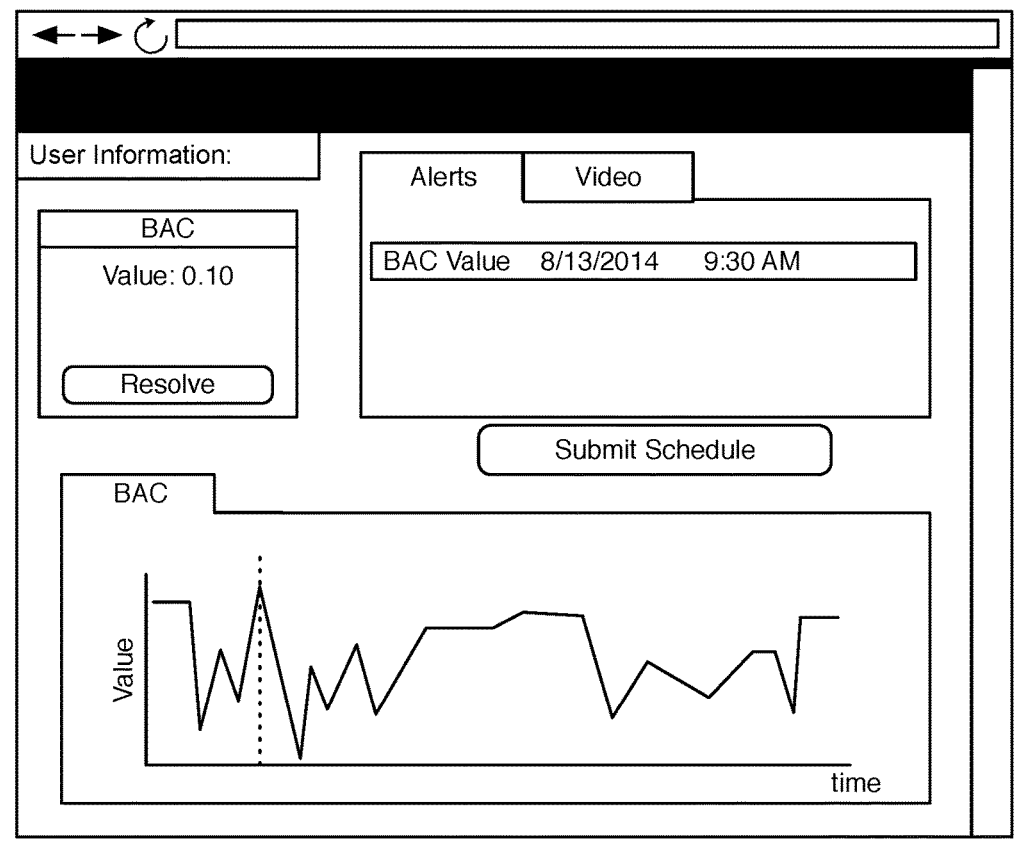

Block S180 recites: transforming the verification assessment and the value of the intoxication metric into an analysis of intoxication of the user, which functions to analyze the user's state of intoxication at the time at which the user provided the breath sample, and additionally to generate an alert if the user's breath sample has been falsified by fraudulent activity. The analysis preferably includes the value of the intoxication metric (e.g., a BAC value for the breath sample), and at least one of the qualitative indication of the user's identity and the quantitative metric characterizing the matching closeness between the user's identifying signature and the authentication signals. In some variations, generating the analysis can include generating a notification that informs the entity of the user's current intoxication state, which in examples informs the entity that the user is: above a legal limit of intoxication, below a legal limit of intoxication, or at an unknown intoxication state relative to a legal limit of intoxication. In Block S180, generating the analysis can include generating a rendering of the analysis, including one or more of: a graphical representation of the user's value of the intoxication metric relative to a legal limit, a trend in the value of the user's intoxication metric over time, and a graphical representation of assurance that the breath sample provided was not a fraudulent sample, examples of which are shown in FIGS. 6A and 6B.

Also shown in FIGS. 1 and 2, the method 100 can include Block S190, which recites: transmitting the analysis to an entity associated with the user for remote monitoring of the user's intoxication. Block S190 functions to provide the analysis to an entity (e.g., a supervising entity) who is at a location remote from the user, in order to facilitate remote monitoring of the user's intoxication. In Block S190, the analysis can be transmitted along with any suitable notification (e.g., visual notification, haptic notification, audio notification, etc.), and can be provided to the entity in any suitable manner (e.g., using a messaging client accessible by the entity, at a mobile device of the entity, etc.). The analysis can be transmitted automatically based upon a given alert state (e.g., an automated notification upon detection that the user is entering a dangerous intoxication state), and/or can be provided when prompted by the user or other entity. In some variations, transmitting the analysis can further enable the entity to assist the user in a given intoxication state, especially when the user is unable to or unwilling to communicate with the entity. In examples, transmitting the analysis can thus allow the entity to locate the user (e.g., based upon GPS data provided along with the transmitted analysis), and can prepare the entity to accommodate the intoxication state of the user (e.g., by sending a taxicab to pick the user up). Additionally or alternatively, transmitting the analysis can further enable the entity to perform a disciplinary action intended to correct behavior of the user and/or prevent future states of impairment or intoxication. The disciplinary action can comprise a form of reprimand, a punishment (e.g., negative report, penalty), or any other suitable disciplinary action. In these examples and variations, the analysis can be transmitted in any suitable manner (e.g., messaging client, by an online social network, in person, etc.), and can be made accessible to the user.

In relation to a supervising entity remotely monitoring the user's intoxication state, as discussed in relation to Block S110 above, variations of Blocks S180 and S190 can include any one or more of: notifying the supervising entity of results of any analysis characterizing impairment of the user (e.g., via a messaging client, upon logging into a secure account intended for access by the supervising entity only); providing time information (e.g., a date, time) pertaining to the breath sample provided by the user, to the supervising entity; rendering content (e.g., image content, audio content, video content, fingerprint scan content, etc.) pertaining to the second authentication signal configured to enable validation of the identity of the user providing the breath sample; and performing any other suitable action that enables the supervising entity to effectively monitor the user's intoxication. In a specific example, the entity can be provided with video content showing the light emission signature and the user, as the user provides the breath sample, which enables validation of the source of the breath sample signal and the identity of the user. Additionally or alternatively, variations of Block S180 and S190 can allow the user to see and/or share (e.g., via a messaging client, via an online social network) content provided to the supervising entity.

The method 100 can, however, include any other suitable blocks or steps configured to facilitate remote monitoring of a user, in relation to states of impairment or intoxication. For instance, the method 100 can include blocks configured to facilitate transmission of incentives (e.g., monetary incentives, motivational incentives, etc.) to individuals, based upon at least one of the verification assessment and the value of the intoxication metric. In one such application, incentive provision can be used to streamline research performed on incentive-based behavior modification for addicts, which can reduce costs and increase efficiencies (e.g., as opposed to having subjects come in for testing and compensation). Additionally or alternatively, applications of the method 100 can be expanded to facilitate remote monitoring of any other suitable type of impairment (e.g., marijuana-induced impairment, other substance-induced impairment, etc.), for instance, in implementing a device configured to analyze samples indicative of substance abuse, as the sample acquisition device. Furthermore, as a person skilled in the art will recognize from the previous detailed description and from the figures and claims, modifications and changes can be made to the method 100 without departing from the scope of the method 100.

2. System

Figure 7:
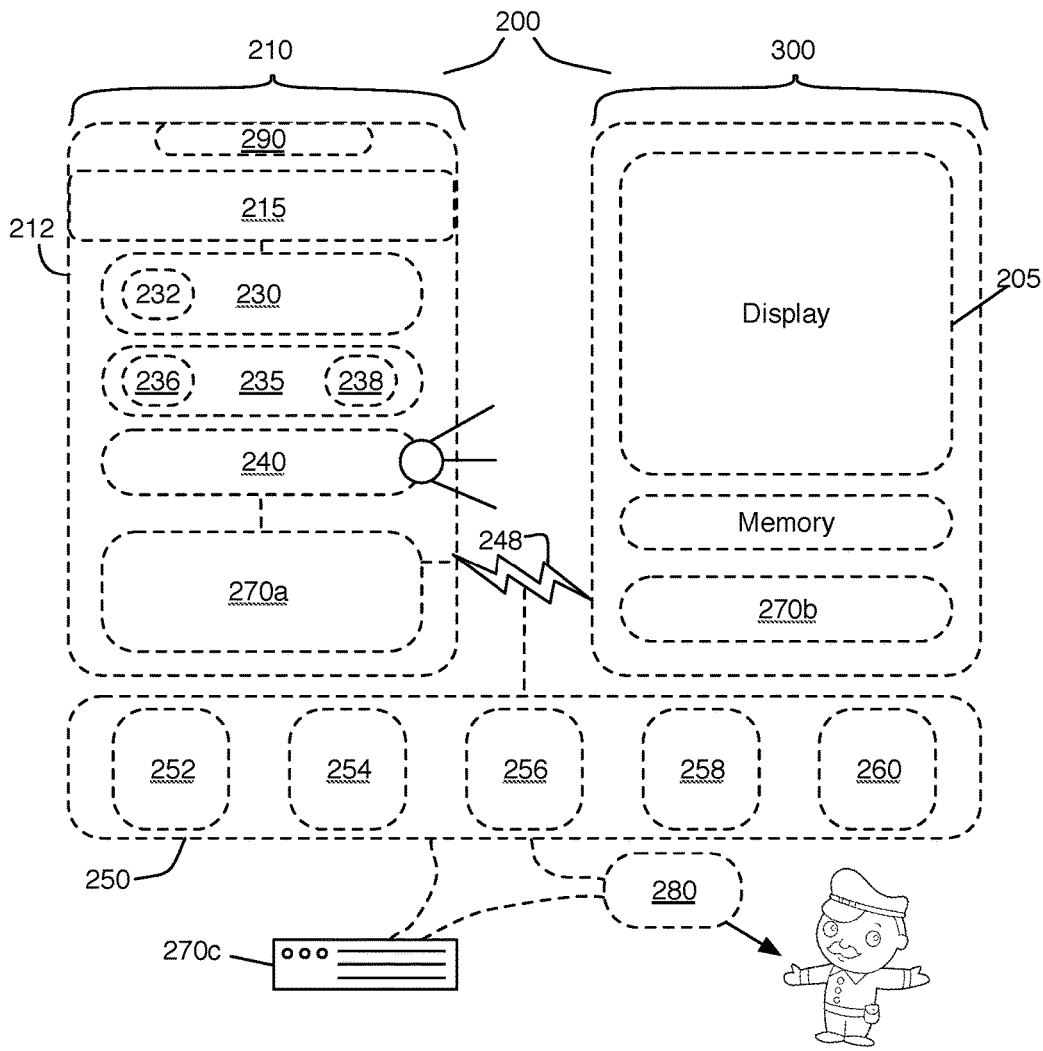
FIG. 7 depicts a schematic of an embodiment of a system for remotely monitoring intoxication.

As shown in FIG. 7, an embodiment of a system 200 for remotely monitoring intoxication of a user includes: a breath sample acquisition device 210 including: a body 212 defining a cavity 215 configured to accept a breath sample from the user, a sample processing module 230 in communication with the cavity 215 and configured to generate a breath sample signal upon reception of the breath sample at a time point, and a user identification module 240 configured to broadcast a unique signature proximal in time to the time point; a data link 248 configured to communicate the breath sample signal; and a processing system 250 in communication with the breath sample acquisition device 210 and including: a first module 252 configured to promote provision of the breath sample by the user at the time point by way of an application executing at a mobile computing device 300, a second module 254 configured to receive the breath sample signal from the breath sample acquisition device 210 by way of the data link 248, and to receive an authentication signal derived from detection of the unique signature with a sensor 305 of the mobile computing device 300, a third module 256 configured to generate a verification assessment that validates provision of the breath sample by the user, based upon the breath sample signal and the authentication signal; a fourth module 258 configured to generate a value of an intoxication metric for the user based upon the breath sample signal; and a fifth module 260 configured to transform the verification assessment and the value of the intoxication metric into an analysis of intoxication of the user. The system 200 can further include any other suitable element that facilitates monitoring of the user's intoxication, such as a storage module 270 configured to store at least one of the verification assessment, the value of the intoxication metric, and the analysis, and a transmission module 280 coupled to at least one of the processing system 250 and the storage module 270 and configured to transmit the analysis to an entity (e.g., a supervising entity).

The system 200 functions to provide a tool that allows an entity to monitor a user's alcohol consumption/intoxication. As such, the system 200 includes elements that cooperate to prevent fraudulent sample submission by users attempting to avoid consequences of an intoxication level above a certain limit (e.g., a legal limit). The system 200 preferably enables an entity who is remote from the user to monitor the user's intoxication levels, such that the user does not need to be in the physical presence of the entity monitoring his/her intoxication. In examples, the entity can be a supervisor (e.g., work supervisor, probation officer, etc.), a caretaker, a family member, an acquaintance, or any other suitable entity associated with the user who has an interest in monitoring the user's intoxication. The system 200 can also incorporate a social component, wherein information related to a user's intoxication can be communicated to another entity using digital and/or non-digital social networks of the user. In variations, the system 200 can be configured to perform at least a portion of the method 100 described in Section 1 above, and can additionally or alternatively be configured to perform any suitable method that facilitates remote monitoring of a user's intoxication.

2.1 System—Sample Acquisition Device

The breath sample acquisition device 210 includes a body 212 defining a cavity 215 configured to accept a breath sample from the user, and functions to provide a module that facilitates reception and processing of the set of breath samples. The body 212 is configured to enclose at least a portion of the system 200, and functions to protect elements of the system 200 over the lifetime usage of the system 200.

Figure 8A:
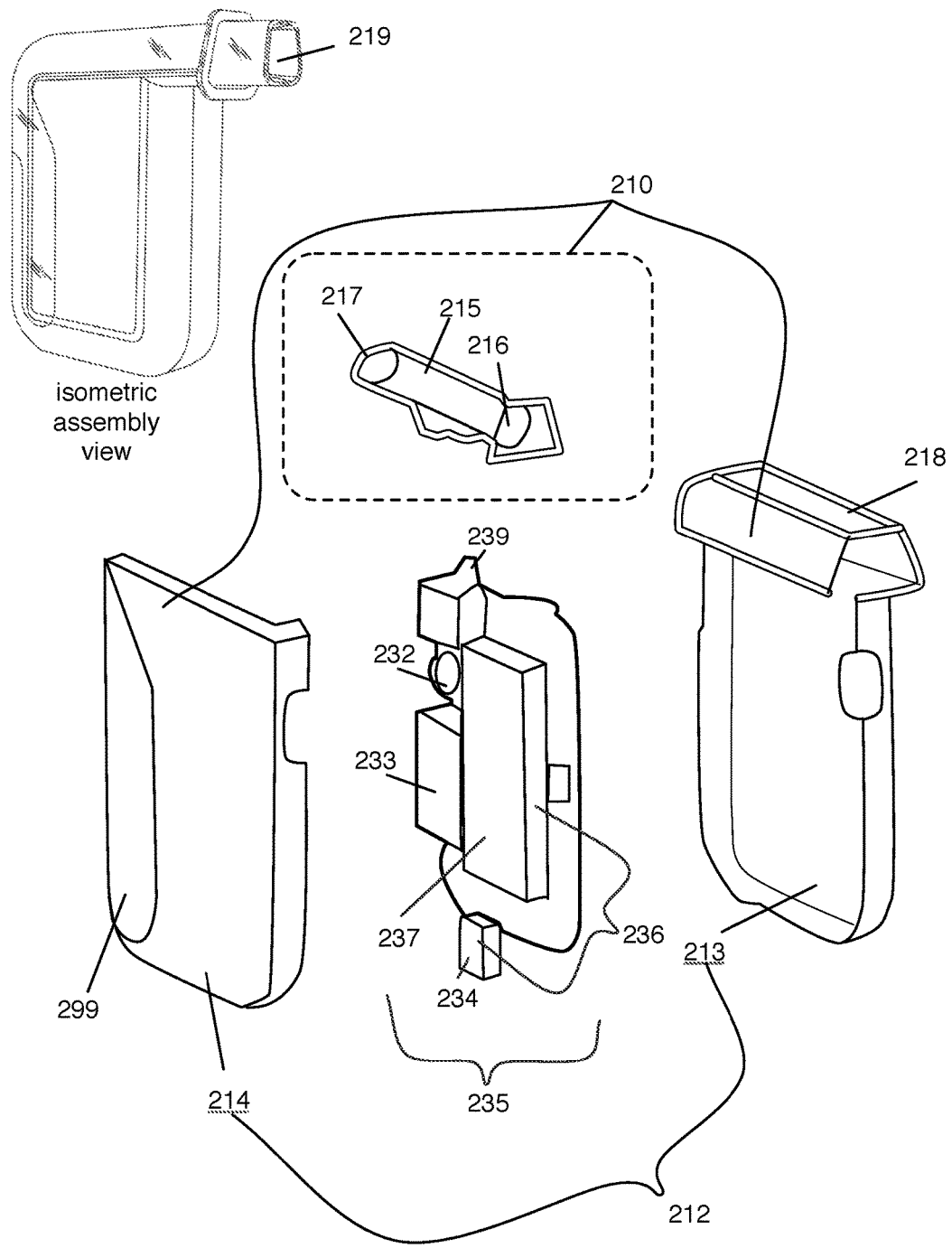
FIGS. 8A and 8B depict views of portions of an example of a system for remotely monitoring intoxication.
Figure 8B:
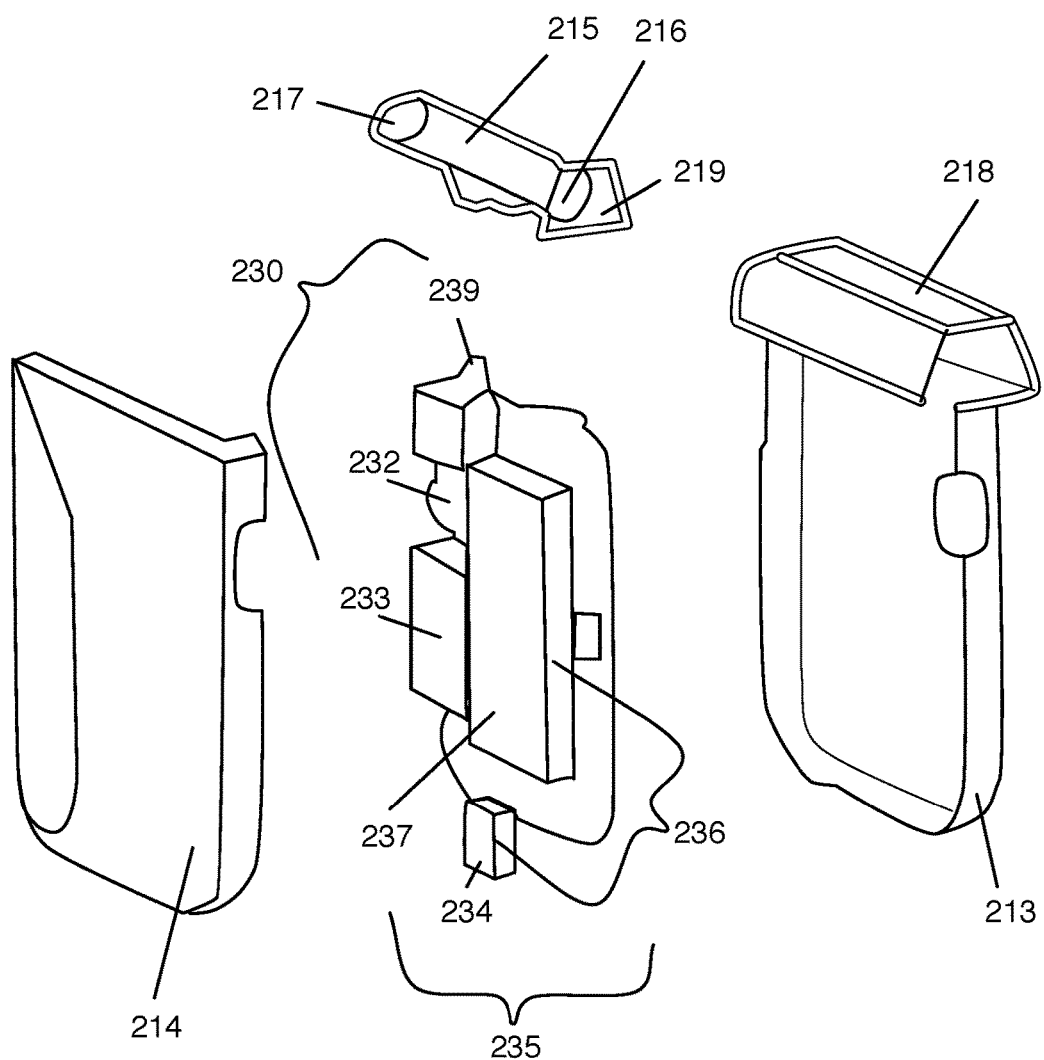

In some embodiments, the body 212 can further function to enhance portability of the system 200, such that the user can conveniently bring the breath sample acquisition device 210 wherever he/she goes. As shown in FIGS. 8A and 8B, the body 212 can include a first body portion 213 and a second body portion 214 coupled together (e.g., by snap fit, by press fit, by couplers, by screws, etc.) to form an interior chamber. In some variations, at least one of the first body portion 213 and the second body portion 214 can include a transparent or translucent portion 299 that allows elements within the body 212 to be visible or identifiable. However, in other variations, the first body portion 213 and the second body portion 214 can be substantially opaque to hide elements within the body 212. The body 212 is preferably composed of a polymer (e.g., polystyrene) that is processed to define features of the body (e.g., by machining, by injection molding, by casting, by printing, etc.); however, the body can alternatively be composed of any other suitable material and processed by any other suitable process. In a specific example, as shown in FIG. 8A, the first body portion 213 and the second body portion 214 couple together by a snap fit to form an approximately rectangular prism with rounded corners, wherein the first body portion 213 includes a transparent portion 299 located at the periphery of the first body portion 213 that allows visualization of elements internal to the body 212.

Figure 9:
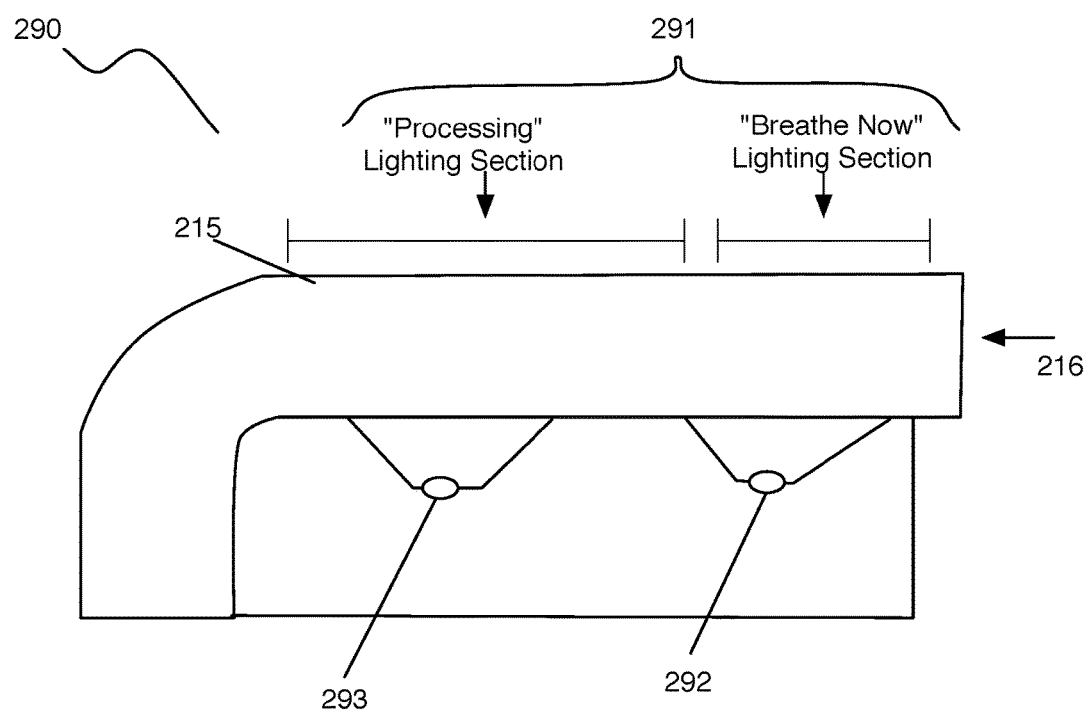
FIG. 9 depicts an example of a portion of a system for remotely monitoring intoxication.

The cavity 215 is preferably included within a portion of the interior chamber of the body 112, is coupled to the sample processing module 130, and comprises a first aperture 216 and a second aperture 217, in communication with the first aperture 216, configured to facilitate sample inflow and outflow. The cavity 215 thus functions to facilitate transmission of a sample from the user to be analyzed by the sample processing module 230. The first aperture 216 and the second aperture 217 can be substantially identical in geometry, such that the cavity has an axis of symmetry (e.g., longitudinal axis of symmetry, transverse axis of symmetry), and such that each of the first aperture 216 and the second aperture 217 can function as both a sample inlet and a sample outlet; however, the first aperture 216 and the second aperture 217 can alternatively be non-identical in geometry or in any other suitable feature, as shown in FIGS. 8A, 8B, and 9, such that the cavity 215 has an orientation that is identifiable by the user and is configured to only receive a sample from one of the first aperture 216 and the second aperture 217.

In one variation, the cavity 215 can be defined by a tube form factor, as shown in FIG. 8A, wherein the cavity 215 defines a substantially linear pathway from the first aperture 216 to the second aperture 217, and wherein the cavity 215 defines a sample intake coupled to the sample processing module 230 at a location between the first aperture 216 and the second aperture 217; however, in other variations, the cavity 215 can alternatively define a non-linear (e.g., curved, boustrophedonic, serpentine, s-shaped, etc.) pathway from the first aperture 216 to the second aperture 217. In still other variations, the cavity 215 can alternatively be defined by any other suitable form factor that facilitates transmission of the sample from the user. The cavity 215 can be of unitary construction with the body 212, can be physically coextensive with the body 212, or can be coupled to the body 212 (e.g., to an interior portion of the body 212, to an exterior portion of the body 212) in any other suitable manner. Furthermore, the cavity 215 is preferably composed of a polymer (e.g., polystyrene) that is processed to define features of the cavity (e.g., by machining, by injection molding, by casting, by printing, etc.); however, the cavity 215 can alternatively be composed of any other suitable material and processed by any other suitable process. Similar to the body 212, the cavity 215 can also include a transparent or translucent portion that can be illuminated (e.g., by a lighting module) to provide an indicator function for the user. In a specific example, as shown in FIGS. 8A and 8B, the cavity 215 is partially coupled to the body 212 by a housing 218 that couples the cavity 212 to a peripheral portion of the body 212, wherein the housing 118 includes apertures that align with and provide access to the first aperture 216 and the second aperture 217.

In some variations, the breath sample acquisition device 210 can further include a mouthpiece 219 configured to mechanically couple (e.g., with protrusions/depressions, with slots, with keys, with tabs, with threads, by press fit, etc.) to at least one of the first aperture 216 and the second aperture 217, in order to facilitate sample reception from the user. The mouthpiece 219 can be configured to permanently couple to at least one of the first aperture 216 and the second aperture 217, semi-permanently couple to at least one of the apertures 216, 217, or reversibly couple to at least one of the apertures 216, 217. Furthermore, the mouthpiece 219 can be processed to define unique identifiers (e.g., colors, textures, geometric features, etc.) that facilitate usage of the system 200 by multiple users. In one specific example, the mouthpiece 219 is configured to be reversibly coupled to the first aperture 216, such that the mouthpiece 219 is a disposable and replaceable element of the breath sample acquisition device 210. In alternative variations of the breath sample acquisition device 210, however, the mouthpiece 219 can be of unitary construction with one of the first aperture 216 and the second aperture 217.

2.2 System—Sample Processing Module

The sample processing module 230 is configured to couple to the cavity 215 of the breath sample acquisition device 210, and functions to facilitate generation of signals from the breath sample that can be transmitted for further analysis. Preferably, the sample processing module 230 receives a metered volume of the breath sample from the user, in order to enable normalization of generated signals indicative of a state of intoxication of the user. In providing a metered volume of the breath sample to the sample processing module 230, the breath sample acquisition device 210 preferably includes a valve that allows a desired volume of the breath sample to pass into the sample processing module 230, in a repeatable and accurate manner. Variations of the sample processing module 230 can, however, operate with or without a metered volume of the breath sample in any other suitable manner.

The sample processing module 230 preferably includes a sensor 232 coupled to an electronics subsystem 235, wherein the sensor 232 interacts with the breath sample and an electronics subsystem 235 in communication with the sample processing module 230 conditions signals produced based upon the sensor-sample interaction for transmission to a processing system 250 for further analysis. The sample processing module 230 is preferably housed within the body 212 of the breath sample acquisition device 210, but can alternatively be configured relative to breath sample acquisition device 210 in any other suitable manner. The sample processing module 230 can, alternatively, include any other suitable elements that facilitate sample processing and transmission.

The sensor 232 is preferably a fuel cell sensor that enables measurement of a user's BAC by an electrochemical process. In particular, the fuel cell sensor is configured to produce an electrical current in response to oxidation of alcohol carried in a breath sample, wherein the magnitude of the produced electrical current varies in a predictable manner according to the amount (e.g., relative volume) of alcohol carried in the breath sample. As such, in some variations, the sensor 232 can be incorporated into a fuel cell subsystem including a pump 233 configured to drive a breath sample received from at least one of the first aperture 216 and the second aperture 217, through a sample intake 239 toward the sensor 232, as shown in FIGS. 8A and 8B.

In other variations, the sensor 232 can alternatively be a semiconductor sensor that produces a change in electrical resistance in response to an alcohol-dioxide reaction, wherein the magnitude of the change in resistance varies in a predictable manner according to the amount (e.g., relative volume) of alcohol carried in the breath sample. In a specific example, the semiconductor sensor can incorporate tin-oxide as a sensing element; however, variations of the semiconductor sensor can alternatively use any other suitable sensing element. In other variations of the sensor 232, the sensor can include a spectrophotometer configured to produce a signal in response to absorbed or emitted light from alcohol molecules carried in the breath sample, or any other suitable type of sensor.

The electronics subsystem 235 comprises a power module 236 configured to power the sample processing module 230 and a conditioning module 238 configured to process signals generated by the sensor 232 for transmission and further analysis. As such, the electronics subsystem 235 functions to provide power to elements of the system 200, condition and/or preprocess signals generated from received breath samples, and facilitate transmission of signals to a processor for further analysis. The electronics system 235 preferably incorporates or is configured to couple to a data link 248 for transmission of signals (e.g., the breath sample signal) from the sample processing module 230 to the processing system 250 for further processing and analysis. Preferably, the electronics subsystem 235 complies with relevant technical and safety standards, such that the system 200 is configured for "home-use"; however, the electronics subsystem can be configured in any suitable manner.

The power module 236 of the electronics subsystem 235 functions to provide regulated and unregulated electrical power to the sample processing module 230 and to allow power storage for the sample processing module 230. The power module 236 preferably comprises a battery 237, such as a lithium-ion battery that is configured to be rechargeable, but can alternatively comprise any other suitable rechargeable battery (e.g., nickel-cadmium, metal halide, nickel metal hydride, or lithium-ion polymer). Alternatively, the power module 236 can comprise a non-rechargeable battery (e.g., alkaline battery) that can be replaced to further enhance modularity in the system 200. The power module 236 can be configured to have any appropriate profile such that the power module 236 provides adequate power characteristics (e.g., cycle life, charging time, discharge time, etc.) for the sample processing module 130 within physical constraints provided by the body 212 of the breath sample acquisition device 210.

In variations where the battery 237 of the power module 236 is rechargeable, the electronics subsystem 235 can also comprise a coil of wire and associated electronics that function to allow inductive charging of the battery by an external power source and the power module 236. Inductive charging provided by the charging coil thus also facilitates patient mobility while interacting with the system 200, such that the patient can be extremely mobile while monitoring his/her intoxication. In alternative variations, however, the charging coil can be altogether omitted (e.g., in variations without a rechargeable battery), or replaced or supplemented by a connection 234 (e.g., USB connection) configured to provide wired charging of a rechargeable battery.

The conditioning module 238 functions to preprocess signals generated by the sensor 232 prior to transmission from the sample processing module 230, and can additionally function to regulate elements of the electronics subsystem 235. The conditioning module 238 preferably comprises signal conditioning elements, including one or more of: an analog-to-digital converter (e.g., to convert analog signals from the sensor 232), an amplifier, and a filter for processing signals prior to transmission. In some variations, the conditioning module 238 can include a microprocessor configured to direct signal conditioning functionalities of the conditioning module 238 and a voltage regulator configured to protect elements of the electronics subsystem 235 from overvoltage and/or under-voltage states.

The electronics subsystem 235 can additionally or alternatively comprise any other suitable element that facilitates intoxication monitoring. Furthermore the electronics subsystem 235 can be coupled to a user control module that interfaces with the electronics subsystem 235, such that manual control of any aspect of the breath sample acquisition device 210 and/or the sample processing module 230 can be performed by the user or any other suitable entity. The user control module can comprise a power toggle (e.g., on/off button) for activating and/or deactivating the breath sample acquisition device 210. The user control module can further include input devices that allow the user to indicate initiation of sample provision. Preferably, the user control module provides a minimal number of controls (e.g., an on/off button, a sample provision initiation button), but can provide any suitable number of manual controls. The user control module can be touch-activated (e.g., with a touch screen, buttons, dials, knobs, sliders), or can be activated using any other suitable manner (e.g., sound activation). Preferably, the user control module is integrated with the electronics subsystem 235, but in other alternative variations, the user control module can be implemented remotely from the system sample processing module 230, for example, using an application executing on a mobile device of the patient.

The data link 248 functions to transmit an output of at least one element of the electronics subsystem 235 to one or more of: a mobile computing device 300, the processing system 250, and any other suitable computing device (e.g., desktop computer, laptop computer, tablet, smartphone, health tracking device, server, cloud). In variations, the mobile computing device 300 can comprise one or more of: a mobile communication device, a head-mounted mobile computing device, a wrist-mounted mobile computing device, and any other suitable computing device associated with the user. Preferably, the data link 248 is a wireless interface; however, the data link 248 can alternatively be a wired connection. In a first variation, the data link 248 can include a Bluetooth module that interfaces with a second Bluetooth module included in the mobile computing device or pair-able element, wherein data or signals are transmitted by the data link 248 to/from the mobile computing device 300 or external element over Bluetooth communications. The data link 248 of the first variation can alternatively implement other types of wireless communications, such as 3G, 4G, radio, or Wi-Fi communication. In the first variation, data and/or signals are preferably encrypted before being transmitted by the data link 248. For example, cryptographic protocols such as Diffie-Hellman key exchange, Wireless Transport Layer Security (WTLS), or any other suitable type of protocol may be used. The data encryption may also comply with standards such as the Data Encryption Standard (DES), Triple Data Encryption Standard (3-DES), or Advanced Encryption Standard (AES).

In a second variation, the data link 248 is a wired connection such that the electronics subsystem 235 can communicate with the mobile computing device and/or any external computing element through a jack of the mobile computing device and/or external computing element. In one specific example of the data link 248 that includes a wired jack, the data link 248 is configured only to transmit output signals from the electronics subsystem 235. In another specific example, the data link 248 is configured to transmit data to and from at least one element of the electronics subsystem 235 and a mobile computing device (e.g., for pairing of the mobile computing device and the electronics subsystem, for synchronization between the mobile computing device and the electronics subsystem). In this example, the data link 248 can transmit output signals into the mobile computing device through the microphone input of the audio jack of the mobile computing device and can retrieve data from the audio output of the audio jack of the mobile computing device. In variations of this example, the data link 248 can additionally or alternatively communicate with the mobile computing device via inter-integrated circuit communication (I2C), one-wire, master-slave, or any other suitable communication protocol. However, the data link 248 can transmit data in any other way and can include any other type of wired connection (such as a USB wired connection) that supports data transfer between the electronics subsystem 235, the mobile computing device, the processing system 250, and/or any other suitable computing element.

2.3 System—User Identification Module

The user identification module 240 is configured to broadcast a unique signature proximal in time to the time point of breath sample provision at the breath sample acquisition device 210. The user identification module 240 preferably implements at least a portion of Blocks S130, S140, and S145 described in Section 1 above; however, the user identification module 240 can additionally or alternatively be configured to implement any other suitable steps. As such, the user identification module 240 functions to facilitate validation of the source (i.e., the sample acquisition device as the source) of the breath sample signal received at the processing system 250. The user identification module 240 preferably includes output elements of the breath sample acquisition device 210, and in examples, can include one or more: light emitting elements (e.g., LEDs) of the sample acquisition device 210, one or more audio signal output elements (e.g., speakers) of the sample acquisition device 210, one or more actuator elements (e.g., vibration motors) of the sample acquisition device 210, and any other suitable output element of the sample acquisition device 210. As noted above, the output elements used to facilitate validation of the source of the breath sample provided by the user are preferably controlled by a control module (e.g., a software module of the mobile computing device paired with the sample acquisition device, a software module of the processing system, etc.), in order to generate the unique signature output by the sample acquisition device 210. Also noted above, characteristics of the unique signature are preferably logged (e.g., at the processing system), in order to enable verification of a match between the anticipated authentication signal logged for future reference, and the actual authentication signal derived from detection of the unique signature.

Also noted above in relation to Block S150 described in Section 1 above, and in relation to the second module 254 of the processing system 250 described below, detection of the unique signature and generation of an authentication signal derived from detection of the unique signature are preferably implemented using a sensor 305 of the mobile computing device 300 in communication with the breath sample acquisition device 210 and the processing system 250; however, detection of the unique signature and generation of the authentication signal can be implemented using any other suitable element.

In relation to validating the identity of the user providing the breath sample, the user identification module 240 is preferably also configured to prompt an action by the user and generate a second authentication signal that enables verification of the identity of the user providing the breath sample, based upon analysis of the action. As such, the user identification module 240 can also function to enable identification of an action performed by the user, as a signature unique to the user, while the user is providing the breath sample, such that signals associated with the action can be used to authenticate the user and prevent fraudulent activity. The action detected by the user identification module 240 is thus preferably performed simultaneously with breath sample provision; however the action detected by the user identification module 240 can be additionally or alternatively be performed prior to (e.g., immediately prior to) and/or after (e.g., immediately after) provision of the breath sample. The user is also preferably able to perform the action with a specific, repeatable, and identifiable configuration/orientation relative to the breath sample acquisition device 210, in order to prevent another entity from providing the breath sample (i.e., a fraudulent breath sample) while the user performs the action. However, in some variations, the user identification module 240 can be configured to adapt to a degree of variation in the user's performance of the action.

In one variation, wherein the user identification module 240 is in communication with the mobile computing device 300, the user identification module 240 can implement an optical sensor (e.g., camera module) configured to capture a feature of the user (e.g., a feature that enables facial recognition, recognition of the user's eye, recognition of the user's ear, recognition of the user's blood vessel network, and/or recognition of the user's dermatological features) as the user provides the breath sample. In this variation, the authentication signals generated can include a signature unique to the user (e.g., the user's facial configuration, the user's eye, the user's ear, the user's blood vessel network, the user's freckles, etc.). In yet another variation, the user identification module 240 can include a reader (e.g., RFID reader, NFC reader, etc.) configured to read an identification chip coupled (e.g., embedded subcutaneously) to the user, wherein the reader is located proximal to the cavity 215 in an orientation that is configured to enable reading of only the identification chip of the user providing the breath sample. In this variation, the authentication signals generated can include a signature unique to the user based upon the information captured in the identification chip (e.g., name, identification number, photograph, fingerprint, parent names and identification numbers, date of birth, gender, address, etc.). In yet another variation, the user identification module 240 can include a module configured to accept a biological sample (e.g., a saliva sample) from the user as the user provides the breath sample, which can be used to authenticate the user (e.g., by analyzing the user's DNA or other biological signature). In yet another example, the user identification module 240 can be configured to prompt the user to ingest a substance that can be detected within the breath of the user, and can include a sensor configured to verify the presence of the substance within the user's breath as the user provides the breath sample. In any of the above variations, the sensor(s) of the user identification module 240 can be fixed relative to the sample-receiving module in a manner that prevents another entity from providing a fraudulent breath sample while the user performs the action.

Additionally or alternatively, in some variations, the user identification module 240 can be coupled to at least one of the breath sample acquisition device 210 and the sample processing module 230, in order to facilitate simultaneous generation of signals from the breath sample and authentication signals resulting from the user's performance of the action. In one variation, the user identification module 240 can prompt the user to make an audible noise (i.e., the action) as the user provides the breath sample, and can include an audio sensor proximal to the cavity 215 of the sample receiving module 230 configured to detect the user's voice, as a unique signature, as the user provides the breath sample. In this variation, the authentication signals generated can include an audio signature unique to the user's voice. In another variation, the user identification module 240 can prompt the user to hum (i.e., the action) as the user provides the breath sample, and can include a vibration sensor (e.g., piezoelectric accelerometer) proximal to the sample receiving module 230 configured to detect the user's hum vibrations, as a unique signature, as the user provides the breath sample. In this variation, the authentication signals generated can include a vibration signature unique to the user's voice. In another variation, the user identification module 240 can prompt the user to touch a fingerprint scanner (i.e., the action) located proximal to the cavity 215 in an orientation that would be difficult to duplicate by another entity as the user provides the breath sample. In this variation, the authentication signals generated can include a fingerprint pattern signature unique to the user.

As such, the user identification module 240 can be implemented using sensors of an electronic device (e.g., mobile computing device, breath sample acquisition device) that can be paired (e.g., wirelessly, in a wired manner) with at least one of the breath sample acquisition device 210 and the sample processing module 230 in order to facilitate simultaneous sample reception and user authentication. In some variations, the electronic device can be further configured to couple (e.g., electromechanically couple, mechanically couple) to at least one of the breath sample acquisition device 210 and the sample preparation module 230, such that the electronic device is fixed relative to one of the breath sample acquisition device 210 and the sample preparation module 230 in a manner that prevents another entity from providing a fraudulent breath sample while the user performs the action. Additional variations can include combinations of the above variations, and/or combinations of the above variations with any other suitable module configured to uniquely identify the user based upon any other suitable user signature.

2.4 System—Processing System

The processing system 250 is in communication with the breath sample acquisition device 210 and includes: a first module 252 configured to promote provision of the breath sample by the user at the time point by way of an application executing at a mobile computing device 300, a second module 254 configured to receive the breath sample signal from the breath sample acquisition device 210 by way of the data link 248, and to receive an authentication signal derived from detection of the unique signature with a sensor 305 of the mobile computing device 300, a third module 256 configured to generate a verification assessment that validates provision of the breath sample by the user, based upon the breath sample signal and the authentication signal; a fourth module 258 configured to generate a value of an intoxication metric for the user based upon the breath sample signal; and a fifth module 260 configured to transform the verification assessment and the value of the intoxication metric into an analysis of intoxication of the user. As such, the processor 250 preferably functions to implement at least a portion of the method 100 described in Section 1 above, but can alternatively be configured to perform any other suitable method that facilitates remote monitoring of the user's intoxication.

The first module 252, the second module 254, the third module 256, the fourth module 258, and the fifth module 260 can be implemented at single processing unit, or can be implemented using multiple processing units. For instance, the modules of the processing system 250 can be implemented in one or more computing systems, wherein the computing system(s) can be implemented at least in part in the cloud and/or as a machine (e.g., computing machine, server, etc.) configured to receive a computer-readable medium storing computer-readable instructions. In one application, a module of the processing system 250 can be implemented in a machine configured to interface directly with the breath sample acquisition device 210 (e.g., using a wired or a wireless connection) to receive the breath sample signal, a module of the processing system 250 can be implemented in a machine configured to interface directly with the mobile computing device 300 (e.g., using a wired or a wireless connection) to receive the authentication signals, and a module of the processing system 250 can be implemented using a cloud-based computing system configured to perform a majority of signal post-processing in relation to the method 100 described above.

2.4 System—Other Elements

The system 200 can additionally further comprise a storage module 270, which functions to retain data generated during use of the system 200. In particular the storage module 270 can be configured to store at least one of the verification assessment, the value of the intoxication metric, and the analysis for further processing or later retrieval. The storage module 270 can be implemented with any one or more of: the electronics subsystem 235, mobile computing device, personal computer, web browser, external server (e.g., cloud), local server, and any combination of the above, in a network configured to transmit, store, and receive data. Preferably, data from the storage module 270 is automatically transmitted to any appropriate external device continuously; however, data from the storage module 270 can alternatively be transmitted intermittently (e.g., every minute, hourly, daily, or weekly). In one example, data generated by any element can be stored on a portion of the storage module 270 when the data link 248 is not coupled to an element external to the electronics subsystem 235. However, in the example, when a link is established between the data link 248 and an external element, data may then be automatically transmitted from the storage module 270. In other examples, the storage module 270 can alternatively be manually prompted to transmit stored data by a user or other entity.

The system 100 can additionally include a transmission module 280 configured to couple to at least one of the processing system 250 and the storage module 270 and which functions to transmit the analysis to an entity for remote monitoring of the user's intoxication. The transmission module 280 can provide the analysis in an electronic format and/or a non-electronic format (e.g., by mail). In some variations, wherein the analysis is provided in an electronic format, the analysis can be accessed using an electronic messaging client provided by a web browser and/or an application (e.g., an application executing at a mobile device of the entity). The transmission module 280 can further implement other functionalities of a mobile device of the entity, such as video and/or audio communication services (e.g., FaceTime, Skype, etc.). As such, the entity may have the option to directly visualize the user as the user performs the action and provides the breath sample, in conjunction with receiving the analysis of the user's intoxication.

As shown in FIGS. 7 and 9, the system 200 can additionally include an indicator module 290, which functions to guide the user in properly providing a breath sample. The indicator module 290 can be implemented using an application executing at a mobile device of the user, and in variations, can incorporate functions of one or more of: a display of the mobile device, an LED of the mobile device, a speaker of the mobile device, a vibration motor of the mobile device, and any other suitable element of the mobile device. In relation to the user identification module 240 described above, the indicator module 290 can share elements with the user identification module 240, such that the elements have dual functionality in guiding the user to provide a breath sample and facilitating authentication of a breath sample received from the user.

In some variations, the indicator module 290 includes a lighting module 291 configured to couple to the breath sample acquisition device 210 and the sample processing module 230. One variation of the lighting module 291 includes a set of light emitting diodes (LEDs) configured to indicate that the user should initiate provision of a breath sample, that the sample processing module 230 is processing the breath sample, and/or that the user has improperly provided a breath sample. In a specific example, as shown in FIG. 9, the lighting module 291 includes a first LED 292 and a second LED 293 oriented proximal to the cavity 215 (e.g., a tube configured to receive the breath sample), such that the first LED 292 and the second LED 293 illuminate the cavity to provide an indicator function for the user. In the specific example, the first LED 292 functions as a visual cue that guides the user in submitting a breath sample into the cavity 215, and the second LED 293 functions as a visual cue that indicates that the sample processing module 230 is currently processing the breath sample provided by the user. As such, the first LED 292 and the second LED 292 in the specific example are both coupled to the electronics subsystem 240 of the sample processing module 230. Other variations of the indicator module 190 can include any other suitable indication elements in communication with any other suitable element of the system 200.

The system 200 can further include any other suitable elements that facilitate remote monitoring of a user's intoxication. Additionally, as a person skilled in the field of intoxication monitoring devices will recognize from the previous detailed description and from the figures and claims, modifications and changes can be made to the embodiments, variations, examples, and specific applications of the system 200 described above without departing from the scope of the system 200.

Variations of the method 100 and system 200 include any combination or permutation of the described components and processes. Furthermore, various processes of the preferred method can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be implemented in the cloud and/or stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for remotely monitoring intoxication of a user, comprising:
   at a first sample acquisition device in communication with a mobile computing device of the user, transmitting a first sample signal, derived from reception of a first sample from the user within a time interval, to the mobile computing device;
   at a second sample acquisition device in communication with the mobile computing device of the user, transmitting a second sample signal, derived from reception of a second sample from the user contemporaneously with the time interval;
   using an imaging sensor of the mobile computing device, generating an authentication signal derived from a sequence of images of the user captured within the time interval;
   at a processing system in communication with the mobile computing device, receiving the first sample signal, the second sample signal, and the authentication signal; and
   generating an intoxication metric, based on the first sample signal, the second sample signal, and the authentication signal.

2. The method of claim 1, wherein the first sample comprises a breath sample, and wherein the second sample comprises a fluid sample collected from a body region of the user in contact with the second sample acquisition device.

3. The method of claim 2, further comprising prompting the user to generate a vibratory input to the first sample acquisition device during provision of the breath sample.

4. The method of claim 1, further comprising detecting a facial characteristic of the user in the sequence of images, and generating the authentication signal based on a comparison of the detected facial characteristic with a database of user facial characteristics.

5. The method of claim 1, further comprising prompting the user to provide fingerprint data at the mobile device within the time interval, and wherein generating the authentication signal is based on the fingerprint data.

6. The method of claim 1, further comprising transmitting a notification to a remote entity in response to the intoxication metric exceeding a threshold value.

7. A method for remotely monitoring intoxication of a user, comprising:
   at a first sample acquisition device in communication with a mobile computing device of the user, transmitting a first sample signal, derived from reception of a first sample from the user within a time interval, to the mobile computing device;
   at a second sample acquisition device in communication with the mobile computing device of the user, transmitting a second sample signal, derived from reception of a second sample from the user contemporaneously with the time interval;
   using a sensor of the mobile computing device, generating an authentication signal that associates the user with the transmitted first sample signal and second sample signal sampled within the time interval;
   at a processing system in communication with the mobile computing device, receiving the first sample signal, the second sample signal, and the authentication signal; and
   generating an intoxication metric based on the first sample signal, the second sample signal, and the authentication signal.

8. The method of claim 7, wherein the first sample comprises a breath sample, and wherein the second sample comprises a fluid sample collected from a body region of the user in contact with the second sample acquisition device.

9. The method of claim 7, wherein the sensor comprises an imaging sensor, wherein generating the authentication signal comprises generating the authentication signal from a sequence of images of the user captured within the time interval at the imaging sensor.

10. The method of claim 9, further comprising detecting a facial characteristic of the user in the sequence of images, and generating the authentication signal based on a comparison of the detected facial characteristic with a database of user facial characteristics.

11. The method of claim 7, further comprising transmitting a notification to a remote entity in response to the intoxication metric exceeding a threshold value.

12. The method of claim 7, wherein the intoxication metric comprises a first portion based on the first sample signal and a second portion based on the second sample signal, and further comprising transmitting a notification to a remote entity in response to the first portion exceeding a first threshold value and a second portion exceeding a second threshold value.

13. The method of claim 7, further comprising prompting the user to generate a vibratory input to the first sample acquisition device during provision of the first sample.

14. The method of claim 7, further comprising prompting the user to provide fingerprint data at the mobile device within the time interval, and wherein generating the authentication signal is based on the fingerprint data.

15. A method for remotely monitoring intoxication of a user, comprising:
   at a first sample acquisition device in communication with a mobile computing device of the user, transmitting a first sample signal, derived from reception of a first sample from the user within a time interval, to the mobile computing device;
   at a second sample acquisition device in communication with the mobile computing device of the user, transmitting a second sample signal, derived from reception of a second sample from the user;
   using an imaging sensor of the mobile computing device, generating an authentication signal derived from a sequence of images of the user captured within the time interval;
   at a processing system in communication with the mobile computing device, receiving the first sample signal, the second sample signal, and the authentication signal; and
   generating an intoxication metric, based on the first sample signal, the second sample signal, and the authentication signal.

16. The method of claim 15, wherein transmitting the second sample signal is performed contemporaneously with the time interval.

17. The method of claim 16, wherein the first sample comprises a breath sample, and wherein the second sample comprises a fluid sample collected from a body region of the user in contact with the second sample acquisition device.

18. The method of claim 16, further comprising prompting the user to generate an auditory input to the second sample acquisition device within the time window.

19. The method of claim 15, further comprising transmitting a notification to a remote entity in response to the intoxication metric exceeding a threshold value.

20. The method of claim 15, further comprising detecting a facial characteristic of the user in the sequence of images, and generating the authentication signal based on a comparison of the detected facial characteristic with a database of user facial characteristics.

* * * * *